United States Patent
Luyten et al.

(10) Patent No.: US 7,371,725 B2
(45) Date of Patent: May 13, 2008

(54) SPONDYLOARTHROPATHIES

(75) Inventors: Frank Luyten, Kraainem (BE); Rik Lories, Linden (BE)

(73) Assignee: K.U. Leuven Research & Development, Leuven (BE)

( * ) Notice: Subject to any disclaimer, the term of this patent is extended or adjusted under 35 U.S.C. 154(b) by 537 days.

(21) Appl. No.: 10/503,751

(22) PCT Filed: Feb. 5, 2003

(86) PCT No.: PCT/BE03/00018

§ 371 (c)(1),
(2), (4) Date: Aug. 5, 2004

(87) PCT Pub. No.: WO03/066081

PCT Pub. Date: Aug. 14, 2003

(65) Prior Publication Data

US 2005/0106144 A1 May 19, 2005

(30) Foreign Application Priority Data

Feb. 5, 2002 (GB) .................... 0202625.0

(51) Int. Cl.
*A61K 38/16* (2006.01)
*A61K 38/17* (2006.01)
*A61K 38/18* (2006.01)
*A61K 38/19* (2006.01)

(52) U.S. Cl. .................. 514/12; 514/2; 514/8
(58) Field of Classification Search .................. None
See application file for complete search history.

(56) References Cited

U.S. PATENT DOCUMENTS 5,843,775 A * 12/1998 Valenzuela et al. ......... 435/325
5,932,216 A  8/1999 Celeste et al.

6,537,966 B1 * 3/2003 Duan et al. .................... 514/2

FOREIGN PATENT DOCUMENTS

| WO | WO 96/01845 | 1/1996 |
|---|---|---|
| WO | WO 98/49296 | 11/1998 |
| WO | WO 99/61044 | 12/1999 |
| WO | WO 00/56879 | 9/2000 |
| WO | WO 02/080952 A | 10/2002 |
| WO | WO 02/080952 A2 | 10/2002 |
| WO | WO 02/100426 | 12/2002 |

OTHER PUBLICATIONS

Massague, 1998, Ann. Rev. Biochem. 67:753-791.*
Natsume et al., "Interaction Between Soluble Type I Receptor for Bone Morphogenetic Protein and Bone Morphogenetic Protein-4," *The Journal of Biological Chemistry*, 272:11535-11540 (1997).
EPO Communication issued in EP Application 03 702 222.5—1216 (dated Aug. 2, 2007).
McGonagle et al., "Enthesitis in spondyloarthropathy," *Current Opinion in Rheumatology* 11:244-250 (1999).
Natsume et al., "Interaction Between Soluble Type I Receptor for Bone Morphogenetic Protein and Bone Morphogenetic Protein-4", *The Journal of Biological Chemistry*, 272:11535-11540 (1997).

* cited by examiner

*Primary Examiner*—Elizabeth C. Kemmerer
(74) *Attorney, Agent, or Firm*—Clark & Elbing LLP

(57) ABSTRACT

The present invention is concerned with a method and composition for use in the medical art. It relates to the prevention and/or minimization of Spondyloarthropathies (SpA) and/or SpA enthesitis. SpA are an important group of chronic inflammatory disorders, affecting both the axial and peripheral skeleton. A particular method and composition optionally including a suitable dispensing device for such compositions can be used for ameliorating or preventing SpA. The invention applies to human and veterinary applications. To date, no single therapeutic approach has proven universally effective in preventing SpA or ameliorating SpA. Therefore, there is a need for compositions and methods which may be used safely and effectively to prevent SpA in a variety of different contexts.

4 Claims, 7 Drawing Sheets

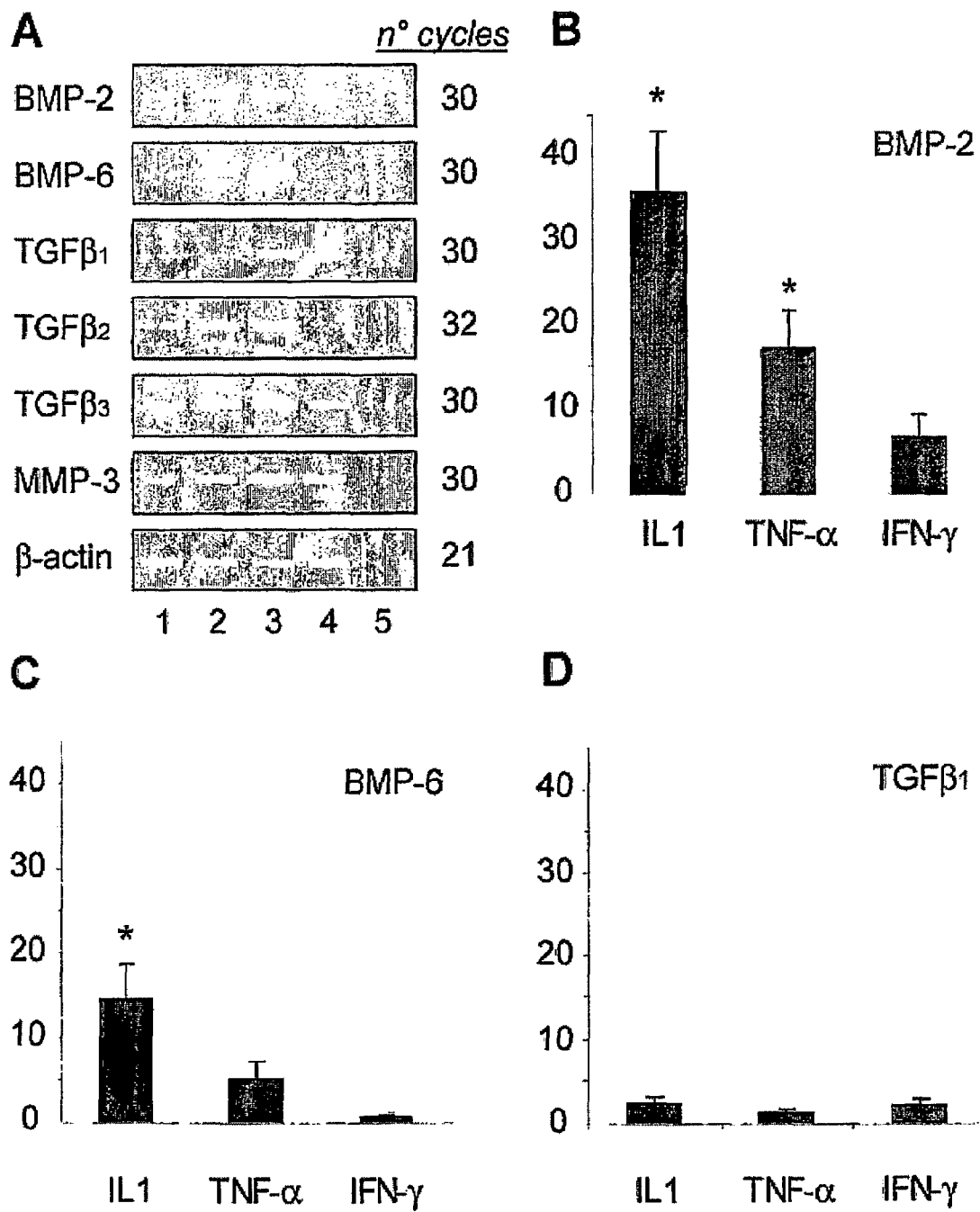
Figure 1 Bone Morphogenetic Proteins (BMPs) are upregulated by pro-inflammatory cytokines.

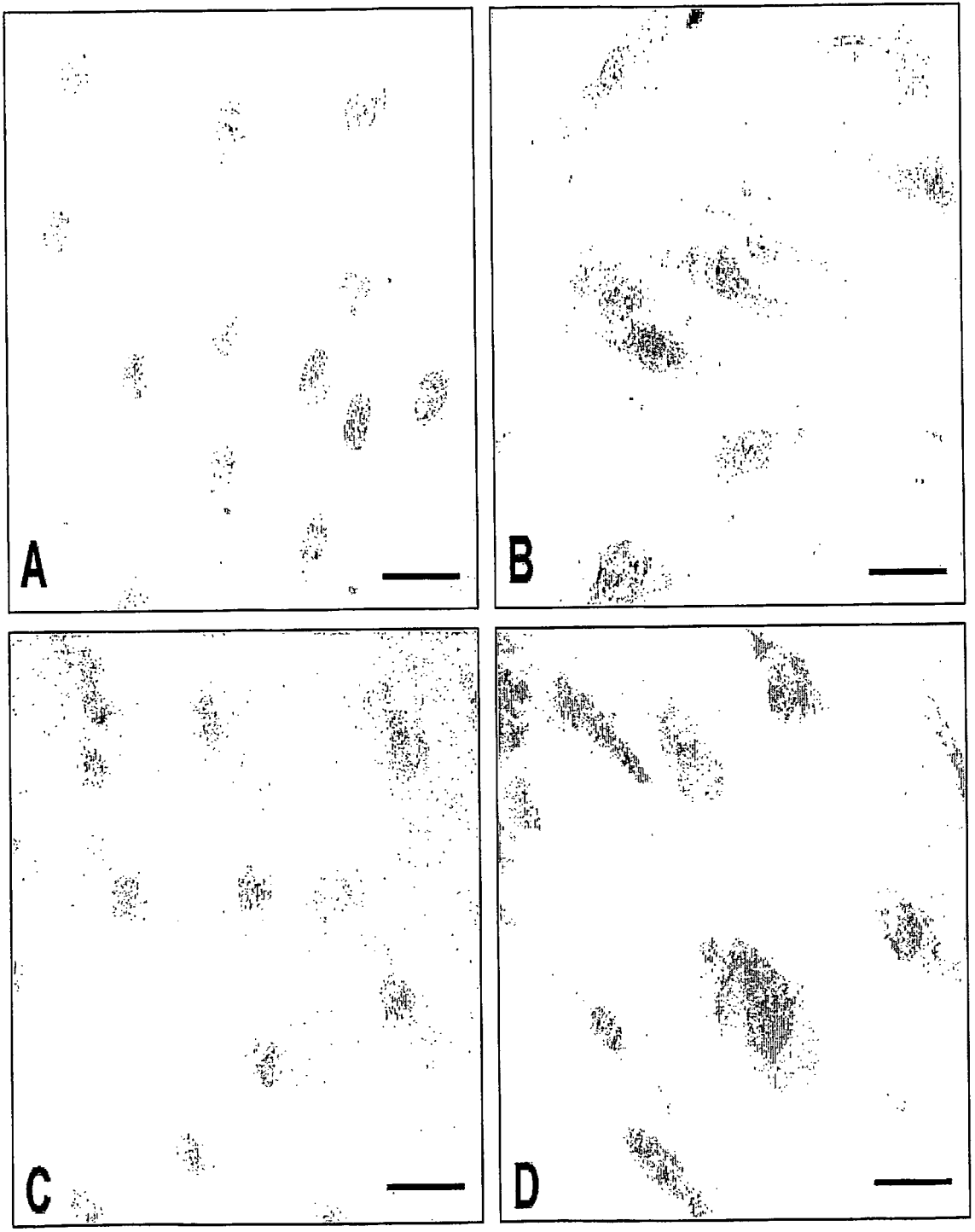
Figure 2 Interleukin (IL)-1β upregulates Bone Morphogenetic (BMP)-2 and BMP-6 protein expression in fibroblast-like synovial cells (FLS).

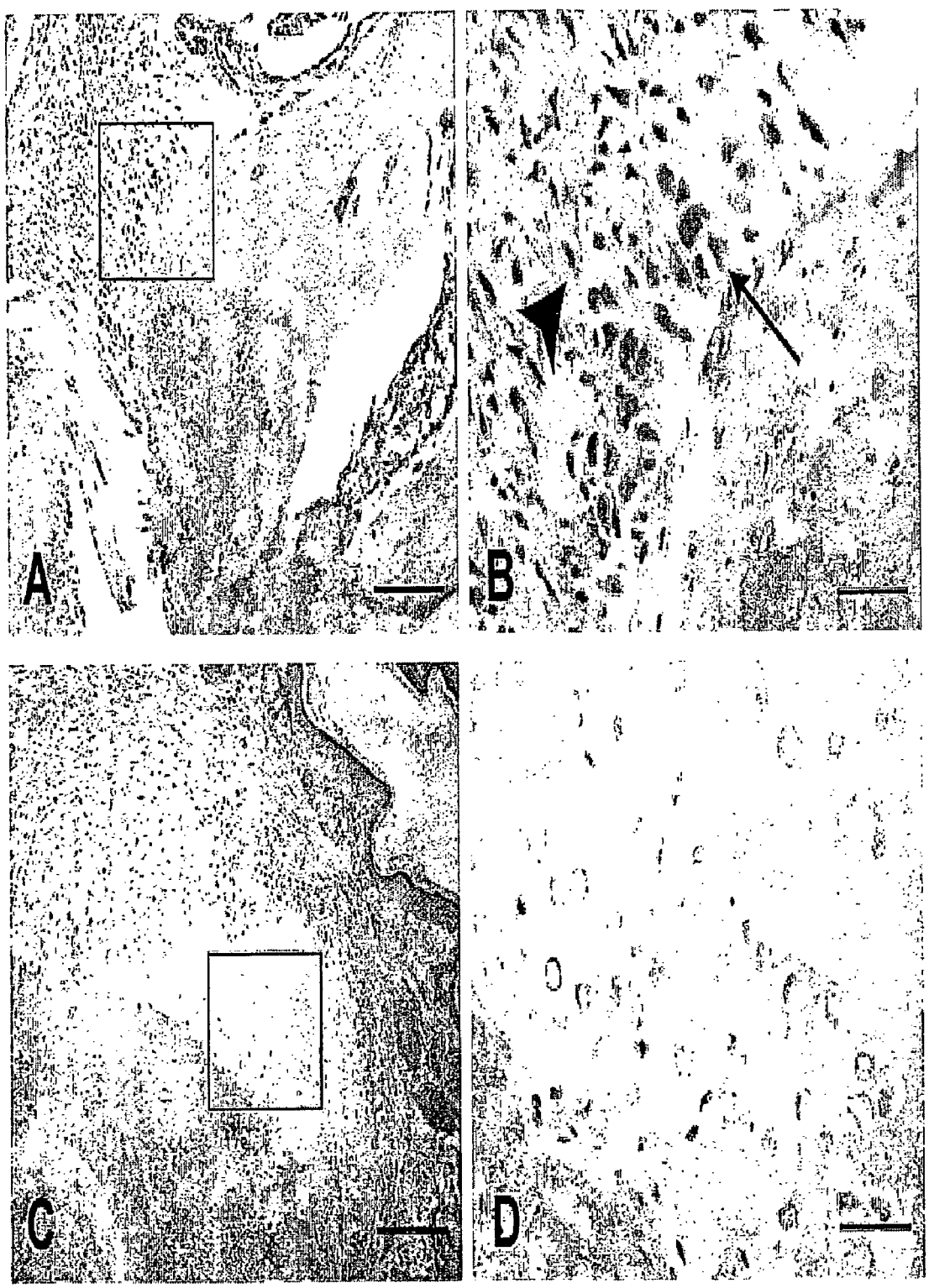
Figure 3 Bone Morphogenetic Protein (BMP)-2 expression in ankylosing enthesitis in DBA/1 mice

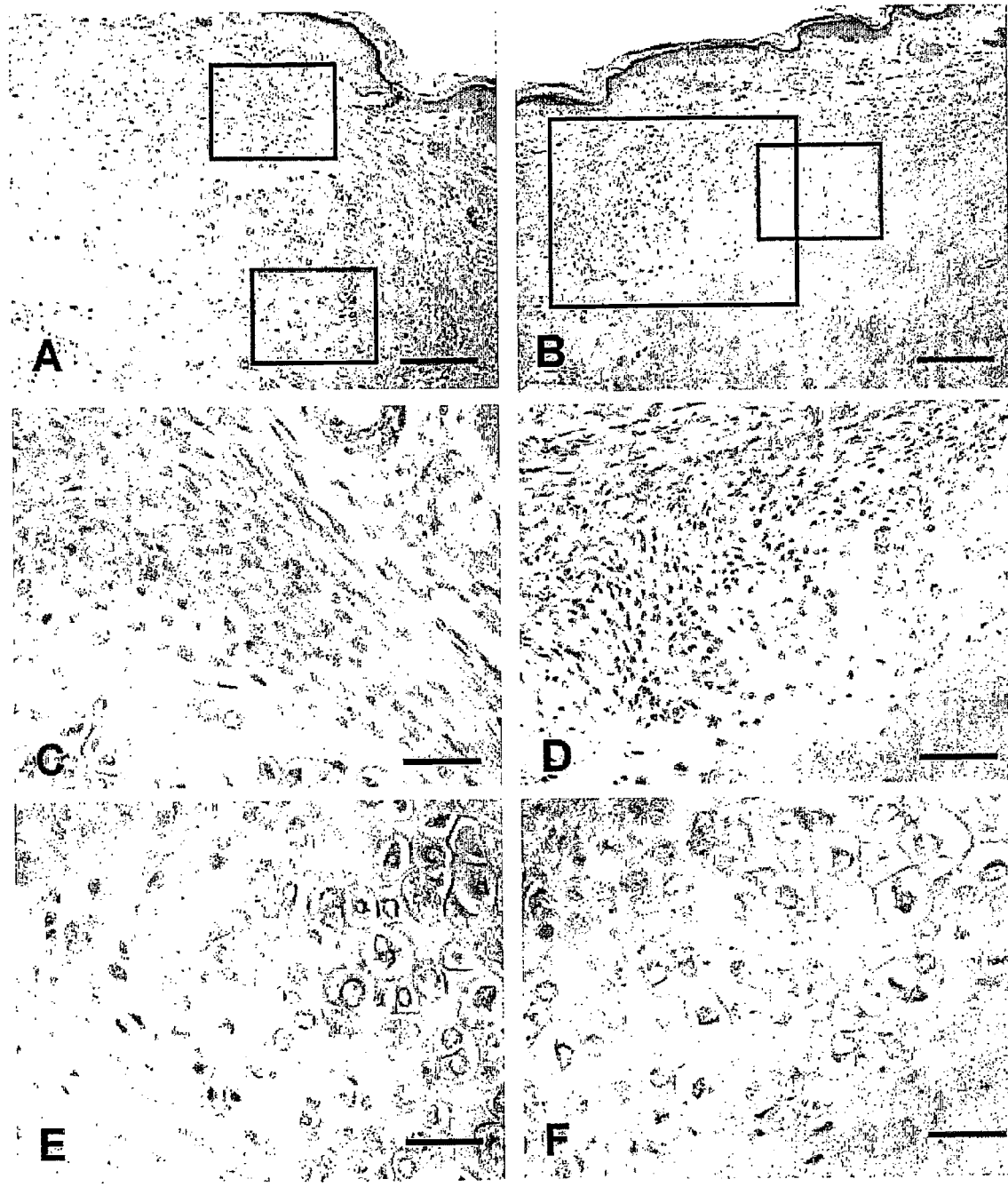
Figure 4 Bone Morphogenetic Protein (BMP)-6 and -7/Osteogenic Protein (OP)-1 expression in ankylosing enthesitis in male DBA/1 mouse

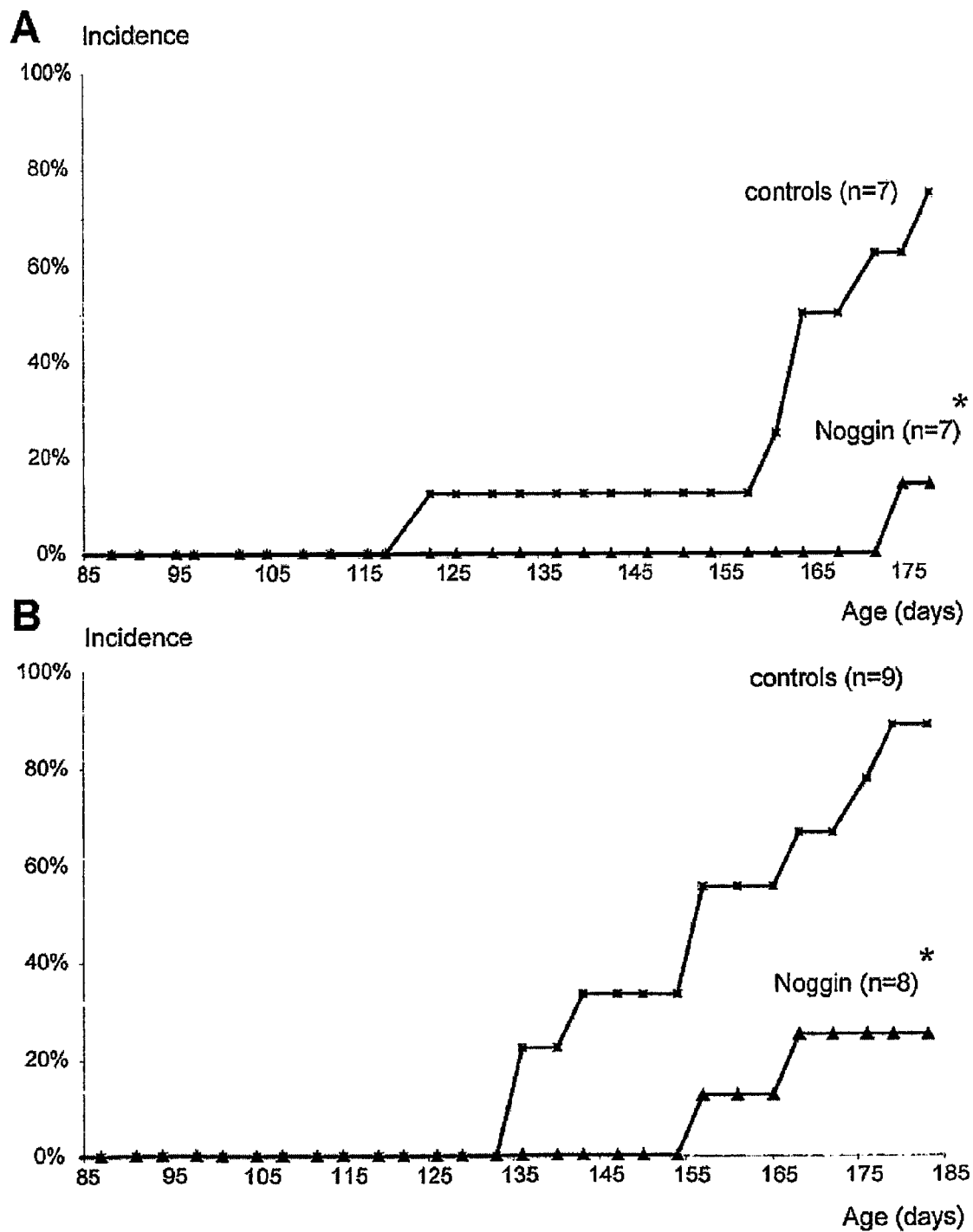
Figure 5 Clinical incidence of arthritis in aging male DBA/1 mice with or without Noggin treatment

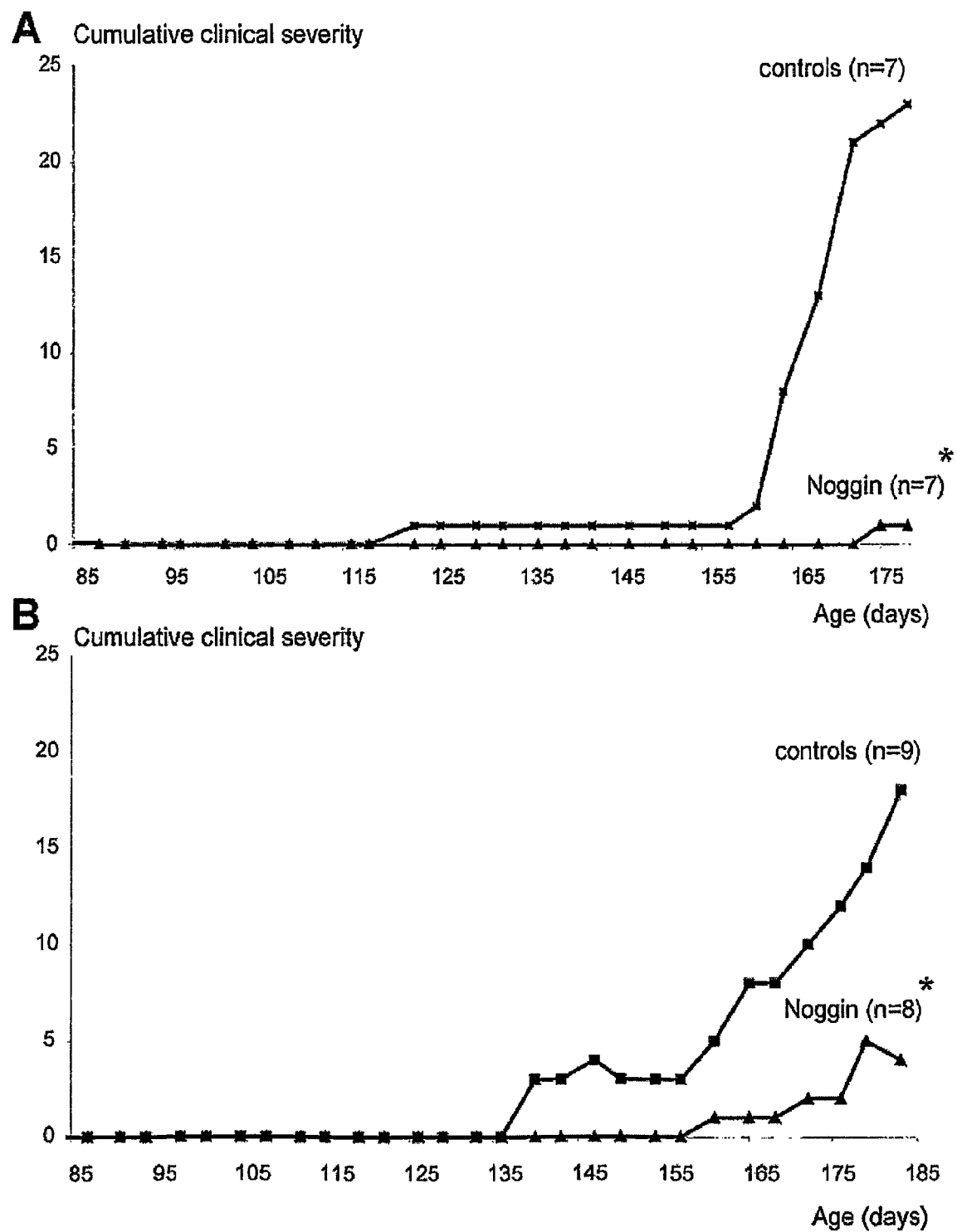
Figure 6 Cumulative clinical severity score of arthritis in aging male DBA/1 mice with or without Noggin treatment

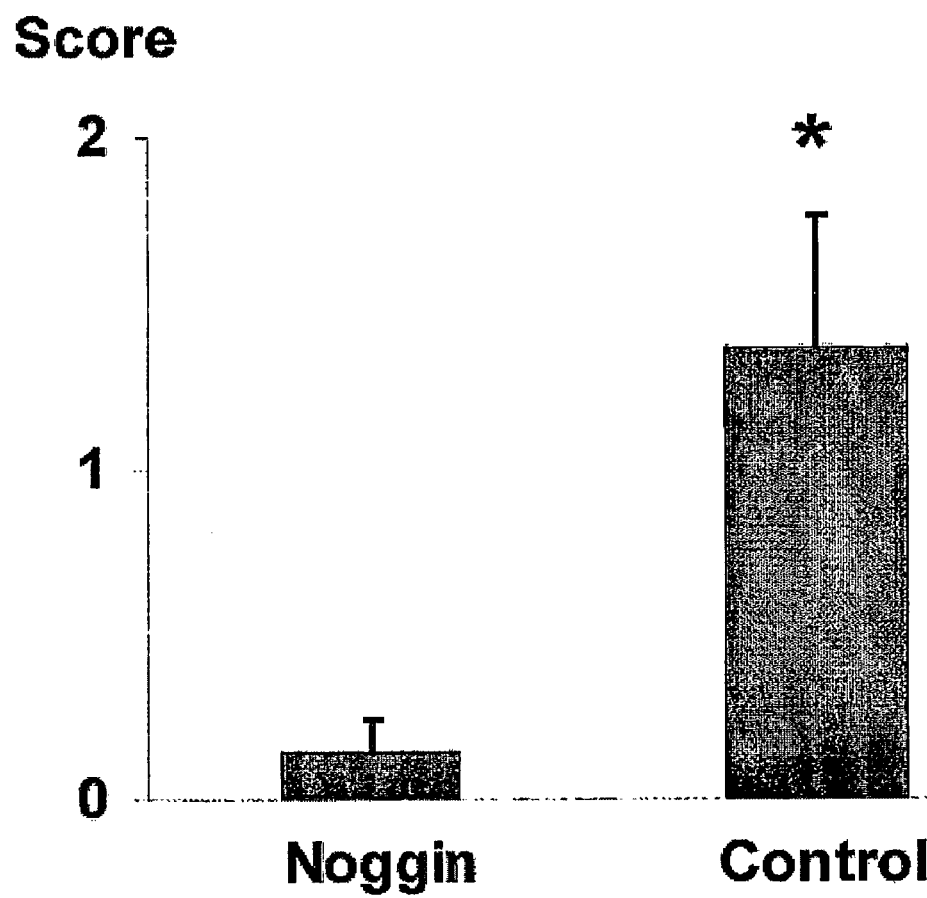
Figure 7 Microscopic disease severity score in arthritis in aging male DBA/1 mice with or without Noggin treatment

SEQUENCE LISTING

```
<160> NUMBER OF SEQ ID NOS: 18

<210> SEQ ID NO 1
<211> LENGTH: 18
<212> TYPE: PRT
<213> ORGANISM: Unknown
<220> FEATURE:
<223> OTHER INFORMATION: peptide sequence conserved cross-species
      (human, mouse, rat, Xenopus)

<400> SEQUENCE: 1

Arg Glu Lys Arg Gln Ala Lys His Lys Ala Arg Lys Arg Leu Lys Ser
1               5                   10                  15

Ser Cys

<210> SEQ ID NO 2
<211> LENGTH: 17
<212> TYPE: PRT
<213> ORGANISM: Homo sapien

<400> SEQUENCE: 2

Thr Gly Ser Lys Gln Arg Ser Gln Asn Arg Ser Lys Thr Pro Lys Asn
1               5                   10                  15

Cys

<210> SEQ ID NO 3
<211> LENGTH: 21
<212> TYPE: DNA
<213> ORGANISM: Artificial
```

```
<220> FEATURE:
<223> OTHER INFORMATION: oligonucleotide

<400> SEQUENCE: 3
gacatcacag ccaccagcaa c                                              21

<210> SEQ ID NO 4
<211> LENGTH: 21
<212> TYPE: DNA
<213> ORGANISM: Artificial
<220> FEATURE:
<223> OTHER INFORMATION: oligonucleotide

<400> SEQUENCE: 4
gaagtagagg acggagatgg c                                              21

<210> SEQ ID NO 5
<211> LENGTH: 21
<212> TYPE: DNA
<213> ORGANISM: Artificial
<220> FEATURE:
<223> OTHER INFORMATION: oligonucleotide

<400> SEQUENCE: 5
caggagcatc agcacagaga c                                              21

<210> SEQ ID NO 6
<211> LENGTH: 21
<212> TYPE: DNA
<213> ORGANISM: Artificial
<220> FEATURE:
<223> OTHER INFORMATION: oligonucleotide

<400> SEQUENCE: 6
atgtgtgcgt tgagtgggaa g                                              21

<210> SEQ ID NO 7
<211> LENGTH: 19
<212> TYPE: DNA
<213> ORGANISM: Artificial
<220> FEATURE:
<223> OTHER INFORMATION: oligonucleotide

<400> SEQUENCE: 7
ttcctggtaa ccgaatgct                                                 19

<210> SEQ ID NO 8
<211> LENGTH: 20
<212> TYPE: DNA
<213> ORGANISM: Artificial
<220> FEATURE:
<223> OTHER INFORMATION: oligonucleotide

<400> SEQUENCE: 8
ggggcttcat aacctcataa                                                20

<210> SEQ ID NO 9
<211> LENGTH: 19
<212> TYPE: DNA
<213> ORGANISM: Artificial
<220> FEATURE:
<223> OTHER INFORMATION: oligonucleotide

<400> SEQUENCE: 9
cagagaccca cccccagca                                                 19
```

-continued

<210> SEQ ID NO 10
<211> LENGTH: 20
<212> TYPE: DNA
<213> ORGANISM: Artificial
<220> FEATURE:
<223> OTHER INFORMATION: oligonucleotide

<400> SEQUENCE: 10
ctgtttgtgt ttggcttgac                                           20

<210> SEQ ID NO 11
<211> LENGTH: 20
<212> TYPE: DNA
<213> ORGANISM: Artificial
<220> FEATURE:
<223> OTHER INFORMATION: oligonucleotide

<400> SEQUENCE: 11
tacccaagag gcatccacac                                           20

<210> SEQ ID NO 12
<211> LENGTH: 20
<212> TYPE: DNA
<213> ORGANISM: Artificial
<220> FEATURE:
<223> OTHER INFORMATION: oligonucleotide

<400> SEQUENCE: 12
cggcaagata cagattcacg                                           20

<210> SEQ ID NO 13
<211> LENGTH: 24
<212> TYPE: DNA
<213> ORGANISM: Artificial
<220> FEATURE:
<223> OTHER INFORMATION: oligonucleotide

<400> SEQUENCE: 13
tccaaagatt taacatctcc aacc                                       24

<210> SEQ ID NO 14
<211> LENGTH: 24
<212> TYPE: DNA
<213> ORGANISM: Artificial
<220> FEATURE:
<223> OTHER INFORMATION: oligonucleotide

<400> SEQUENCE: 14
tcccactgtt tttttccta gtgg                                        24

<210> SEQ ID NO 15
<211> LENGTH: 24
<212> TYPE: DNA
<213> ORGANISM: Artificial
<220> FEATURE:
<223> OTHER INFORMATION: oligonucleotide

<400> SEQUENCE: 15
cagaaataca gcaacaattc ctgg                                       24

<210> SEQ ID NO 16
<211> LENGTH: 24
<212> TYPE: DNA
<213> ORGANISM: Artificial
<220> FEATURE:
<223> OTHER INFORMATION: oligonucleotide -continued

```
<400> SEQUENCE: 16
ttgcagtgtg ttatccctgc tgtc                                              24

<210> SEQ ID NO 17
<211> LENGTH: 30
<212> TYPE: DNA
<213> ORGANISM: Artificial
<220> FEATURE:
<223> OTHER INFORMATION: oligonucleotide

<400> SEQUENCE: 17
tgacggggtc acccacactg tgcccatcta                                        30

<210> SEQ ID NO 18
<211> LENGTH: 30
<212> TYPE: DNA
<213> ORGANISM: Artificial
<220> FEATURE:
<223> OTHER INFORMATION: oligonucleotide

<400> SEQUENCE: 18
ctagaagcat ttgcggtgga cgatggaggg                                        30
```

SPONDYLOARTHROPATHIES

CROSS REFERENCE TO RELATED APPLICATIONS

This application is the U.S. National Stage of International Application No. PCT/BE03/00018, filed Feb. 5, 2003, which was published in English under PCT Article 21(2), and which claims the benefit of GB 0202625.0, filed Feb. 5, 2002, the disclosure of which is hereby incorporated by reference.

FIELD OF THE INVENTION

The present invention is concerned with a method and composition for use in the medical art. It relates to the prevention and/or treatment of Spondyloarthropathies (SpA) and/or SpA enthesitis. SpA is an important group of chronic inflammatory disorders, affecting both the axial and peripheral skeleton. A particular method and composition can be used for ameliorating or preventing SpA and/or SpA enthesitis.

BACKGROUND OF THE INVENTION

To date, no single therapeutic approach has proven universally effective in preventing SpA or ameliorating SpA. Therefore, there is a need for compositions and methods that may be used safely and effectively to prevent or treat SpA in a variety of different contexts. The invention applies to human and veterinary applications.

The Spondyloarthropathies (SpA) are an important group of chronic inflammatory disorders, affecting both the axial and peripheral skeleton. Within the SpA group, several entities are recognized: Ankylosing Spondylitis (AS), Psoriatic Arthritis (PsA), Enteropathic Arthritis or Arthritis associated with inflammatory bowel disease (IBD-SpA), Reactive Arthritis (ReA) including Reiter's syndrome and the undifferentiated forms (UspA) and, possibly, also Whipple disease and Behcet disease. (John H. Klippel, et al., Rheumatology Mosby Saint Louis (Ill.) Publ Jaar: 1994 Ed. by John H. Klippel and Paul A. Dieppe.)

These diseases can be easily classified into the SpA group since they display a number of striking similarities: enthesitis, strong genetic predisposition in HLA-B27 positive individuals, involvement of the sacroiliacal and intervertebral joints, asymmetrical oligoarthritis in the peripheral joints mainly affecting the lower limbs. Enthesitis, leading to neochondro- or neo-osteogenesis and joint ankylosis, is the hallmark feature of all forms of SpA affecting synovial joints (e.g. knee joint), cartilaginous joints (e.g. discovertebral junction), syndesmoses (e.g. upper part of the sacroiliacal joints) and extra-articular enthesis (e.g. insertion of the Achilles tendon) (Ball J., Ann Rheum Dis. 1971 May; 30(3):213-23; Benjamin M. and McGonagle D., J Anatomy 2001; 199(5):503-526).

A therapy aimed at disrupting the enthesial process of proliferation, differentiation, cartilage and bone formation leading to ankylosis, is currently lacking. The actual treatment is solely aimed at controlling the inflammatory process by using steroids, non-steroidal anti-inflammatory drugs and second-line antirheumatic immunomodulatory drugs, all with limited success and/or considerable side-effects without specific interference with the process of cartilage and bone formation. Presently, for end stage refractory diseases, surgical management in the form of for example hip replacement is advised. Therefore the need for specific treatments of ankylosing enthesitis remains high.

The present invention embodies that specific morphogens such as Bone Morphogenetic Protein (BMPs) including BMP-2, BMP-6 and BMP-7 play a key role in steering the pathological process leading to joint ankylosis. There are now known to be at least 15 members of the family of the BMP's; all except BMP-1 have been classified as members of the transforming growth factor-β (TGF-β) superfamily. The TGF-β superfamily is a large group of structurally related polypeptides, capable of regulating a wide array of cellular processes such as proliferation, differentiation, lineage determination, motility, adhesion and death. BMP-7 has previously been shown to possess anti-inflammatory properties (Vukicevic, S. et al., Journal of Clinical Investigation 1998; 102 (1): 202-214; Maric, I. et al. Abstract 4th International Conference on BMPs, Oct. 17-21, 2002, Sacramento, Calif.).

The invention therefore embodies the specific treatment of SpA or SpA enthesitis by using inhibitors of BMPs, or related family members, such as Noggin, Chordin, Gremlin and Follistatin, or cellular therapies directed against these specific morphogens. Treatment aimed at blocking these morphogens can be both locally administered as well as systemically. Chordin, for instance, binds to BMP-2 and BMP-4 in the extracellular space, blocking the interaction of BMPs with their receptor.

Another embodiment of the present invention relates to the use of molecules that can neutralize the activity of BMPs by interfering with its synthesis, formation, translation, transcription, receptor binding and/or receptor binding mediated signal transduction, for the treatment or prevention of SpA or SpA enthesitis.

A strikingly simple signaling pathway is used by BMPs and related factors (for review see Massague, J. Annu Rev. Biochem. 1998; 67: 753-791; Massague, J. Nat. Rev. Mol. Cell. Biol. 2000; 1:169-178). The enormous diversity of cellular responses is achieved by regulatory mechanisms on all levels of this pathway. The dimeric ligand assembles a receptor complex consisting of two different receptor serine/threonine kinases (type I and type II receptors). The type II receptor phosphorylates the type I receptor, resulting in the activation of this receptor kinase. The type I receptor subsequently phosphorylates specific receptor substrates (Smad molecules in vertebrates, Mad in *Drosophila*). The phosphorylated receptor-Smad (R-Smad) associates with common Smad-4 and translocates to the nucleus. The Smad complexes have DNA binding and transcriptional activity.

Vertebrate type I receptors can be divided into three groups. One group includes the TGFβ type I receptor (TβRI), formerly known as Activin-receptor like kinase-5 (ALK-5), Activin-receptor type Ib (ActRIb) or ALK-4 and ALK-7. The second group includes BMPRIa (ALK-3) and BMPRIb (ALK-6). The third group includes ALK-1 and ActRIa (ALK-2). Similar type I receptors are found in invertebrates: In vertebrates the type II receptors include TβRII, BMPRII, ActRIIa and ActRIIb.

Regarding the binding of BMPs with recptors, ActRI is binding BMP-2, BMP-6 and BMP-7 (Ebisawa et al. J. Cell. Sci. 1999; 112: 3519-3527) with BMPRII, and ActA, BMP-6 and BMP-7 with ActRII. BMPRIa is binding BMP-2 with ActRIIB. BMP-2, -4 and -7 are binding BMPRIb and BMPRII.

Most ligands interact with the receptors as homodimers. However, the existence of TGFβ (Ogawa, Y. et al. J. Biol. Chem. 1992; 267: 2325-2328) and Activin heterodimers (Ling, N. et al. Nature 1986; 321: 779-782) has been documented. BMP heterodimers have been constructed in vitro (Aono, A. et al. Biochem. Biophys. Res. Commun. 1995; 210: 670-677) but have not been demonstrated in vivo. TGFβ and Act type I receptors only bind ligands bound to type II receptors (Laiho, M. et al. J. Biol. Chem. 1990; 265: 18518-18524), BMP type I and type II receptors bind ligand with high affinity when expressed together and with low affinity when expressed separately (Liu, F. et al. Mol. Cell Biol. 1995; 15: 3479-3486).

The BMP receptors use Smad1, Smad5 and Smad8 as substrates and specific DNA-binding co-factors (FAST, OAZ, Mixer and Milk), as well as other transcription factors such as AP-1 and AML proteins (Massague, J. et al. Genes Dev. 2000; 14: 627-644) and additional co-activators (p300/CBp) or co-repressors (TGIF, c-Ski and SnoN) for interaction with genes.

FKBP12 is a cytosolic protein enhancing cytosolic calcium release and inhibiting TGFβ type I receptors by blocking TGFβ type II induced type I receptor phosphorylation (Chen, Y. G. et al. EMBO J. 1997; 16: 3866-3876). BMP receptor associated molecule-1 (BRAM1) may have a similar function on BMPRIa (Kurozumi, K. et al. Genes Cells 1998; 3: 257-264). BAMBI (BMP and activin membrane-bound inhibitor) was identified as a BMP inhibitor in Xenopus, hindering BMP—receptor heterodimerisation (Onichtchouk, D. et al. Nature 1999; 401: 480-485). A human homologue nma has also been identified (Wordinger, R. J. et al. Mol. Vis. 2002; 8: 241-250). Screening has identified several other receptor interacting proteins such as TRIP-1, STRAP, PP2A and TRAP-1, but their precise functions remains to be elucidated.

Inhibitors, antagonists, receptor and Smad modulation, as well as inhibitory Smads (Smad6 and Smad7) modulate BMP signaling pathways. Many antagonists of BMP signal transduction are already known in the art and they include Fetuin glycoprotein, also known as α2-HS glycoprotein in humans, Noggin and Chordin. Noggin, a 32 kD glycoprotein (Smith, W. C. et al. Cell 1992; 70: 829-840) and Chordin, a 120 kD molecule related to thrombospondin-1 (Francois, V. et al. Cell 1995; 80: 19-20), are secreted proteins specifically antagonizing BMP activity by blocking BMP interaction with cell surface receptors. Short gastrulation (Sog) is the *Drosophila* homologue of Chordin.nhibiting Dpp (protein encoded by the decapentaplegic gene). Noggin displays specificity, characterised in that binding is very tight to BMP-2 and BMP-4 (Kd=2×10$^{-11}$ M) and weaker to BMP-5, BMP-6 and BMP-7. Fetuin has been shown to block osteogenesis, a function promoted by BMP, in a culture of rat bone marrow cells and that a Fetuin derived peptide binds BMP 2 (M. Demetriou et al., J. Biol. Chem. 1996; 271: 12755-61.) The DAN family of BMP antagonists, containing vertebrate DAN, Dante, Gremlin, Cerl and 'Protein Related to DAN and Cerberus' (PRDC), as well as *Xenopus* Cerberus, Chick caronte and *C. elegans* CdCanl, also prevent interaction of BMPs with signaling receptors (Hsu, D. R. et al. Mol. Cell. 1998; 1: 673-683). Follistatin is a secreted glycoprotein that antagonizes Activin, but that also binds some BMPs (Iemura, S. et al. Proc. Natl. Acad. Sci. U.S.A. 1998; 95: 9337-9342). Latency-associated protein is in fact the TGFβ propeptide non-covalently bound to the mature polypeptide inhibiting TGFβ receptor interaction (McMahon, G. A. et al. Biochem. J. 1996; 313: 343-351).

SUMMARY OF THE INVENTION

The invention provides a method of treating or preventing SpA or of treating or preventing SpA enthesitis by inhibiting BMP, antagonising the function of a Bone Morphogenetic Protein (BMP) or related protein member, which comprises interfering with the synthesis or formation of BMP, contacting said BMP with a proper ligand or contacting their receptor with a proper ligand, or by modulating the BMP signaling pathway.

ILLUSTRATIVE EMBODIMENT OF THE INVENTION

Brief Description of the Figures

FIG. 1: Bone Morphogenetic Proteins are upregulated by pro-inflammatory cytokines.

BMP-2 and BMP-6, not Transforming Growth Factor (TGF)β1 gene expression is upregulated by Tumor Necrosis Factor (TNF)-α and Interleukin (IL)-1β, not by Interferon (IFN)-γ. FLS at confluence were further cultured for 24 hours with growth medium, or stimulated for 24 hours with TNF-α (10 ng/ml), IL-1b (10 ng/ml) or IFN-γ (100 U/ml). (A) Semiquantitative RT-PCR analysis, lanes:control (1), TNF-α (2), IL-1β (3), IFN-γ (4), Milli-Q water (5). (B-D) Real-time quantitative RT-PCR of BMP-2 (B), BMP-6 (C) and TGFβ1 (D) gene expression. Gene expression levels were normalized for the expression of the housekeeping gene b-actin and compared to non-stimulated controls. Milli-Q water was used as a template negative control. Results are from 12 different experiments using cells from 4 different donors (mean+SEM) (*p<0.05).

FIG. 2. Interleukin (IL)-1β upregulates Bone Morphogenetic Protein-2 and BMP-6 protein expression in fibroblast-like synovial cells (FLS).

Normal FLS were cultured in tissue culture slides. At confluence FLS were cultured in growth medium alone (A-C) or stimulated for 24 hours with IL-1β (10 ng/ml) (B-D). BMP-2 (A-B) and BMP-6 (C-D) were visualized by immunohistochemistry. (Bar=25 μm).

FIG. 3. Bone Morphogenetic Protein-2 expression in ankylosing enthesitis in DBA/1 mice.

(A-B) BMP-2 expression in early proliferative stages of ankylosing enthesitis. BMP-2 positive cells are recognized in the enthesis (large round shaped chondrocyte-like cells) (arrow) but also in more spindle shaped fibroblast-like cells (arrowhead) (hematoxilin counterstaining; Bar=200 mm (A); Bar=50 mm (B)).

(C-D) BMP-2 expression is not detected in later stages of ankylosing enthesitis in particular in hypertrophic chondrocyte-like cells (hematoxilin counterstaining; Bar=200 mm (C); Bar=50 mm (D)).

FIG. 4. Bone Morphogenetic Protein-6 and -7/Osteogenic Protein (OP)-1 expression in ankylosing enthesitis in male DBA/1 mouse.

(A-C-E) BMP-6 expression in cartilage matrix and hypertrophic chondrocytes. (hematoxilin counterstaining; (A) Bar=200 mm, (C-E) Bar=50 mm).

(B-D-F) BMP-7/OP-1 expression in pre-hypertrophic chondrocytes. In hypertrophic chondrocytes no BMP-7 positivity is seen. (hematoxilin counterstaining; (B) Bar=200 mm, (D) Bar=100 mm; (F) Bar=50 mm).

FIG. 5. Clinical incidence of arthritis in aging male DBA/1 mice with or without Noggin treatment.

Two separate experiments are shown (A and B). Animals were treated with Noggin cDNA injections or empty control vectors. In both experiments Noggin treatment resulted in a significantly lower incidence of arthritis (*Gehan's Wilcoxon test p<0.5).

FIG. 6. Cumulative clinical severity score of arthritis in aging male DBA/1 mice with or without Noggin treatment.

Two separate experiments are shown (A and B). Animals were treated with Noggin cDNA injections or empty control vectors. In both experiments Noggin treatment resulted in a significantly lower clinical severity of arthritis (*Mann Whitney U test p<0.5).

FIG. 7. Microscopic disease severity score in arthritis in aging male DBA/1 mice with or without Noggin treatment.

Animals were treated with Noggin cDNA injections (n=7) or empty control vectors (n=7). Noggin treatment resulted in a significantly lower microscopic disease severity score as compared to controls. (mean+SEM; *Mann Whitney U test p<0.05).

DEFINITIONS

Enthesis refers to the insertion of a tendon, ligament, capsula or fascia into bone. Some authors advocate the inclusion of the junction between cartilage and subchondral bone into the enthesis concept (Francois R J et al., Curr Opinion Rheumatol 2001; 13(4): 255-264). We are supporting this broader enthesitis concept. Although the bone-cartilage junction seems anatomically different, from a developmental viewpoint all these regions can be described as border zones between mesenchymal musculoskeletal tissues with close contact between the collagenous fibers irradiating into each other.

The enthesitis as seen in SpA is clearly different from all other types of enthesopathy. Therefore the term SpA enthesitis is used in this application. In traumatic enthesopathy the structural integrity of the enthesis is abruptedly disturbed resulting e.g. in tendon or ligament rupture. In degenerative enthesopathy, some degradation of the fiberstructure is seen, resulting in the formation of bony spurs. However these lesions seldom cause any symptoms. In SpA enthesitis, the cell proliferation and local edema is causing specific symptoms characteristic for an inflammatory disorder. Pathological studies of SpA enthesitis are rare, given the practical and ethical problems in obtaining tissue specimens. Also it is not clear what actually causes the disease. The pathological sequence of events can be summarized as follows. In a first phase, a pauci-inflammatory reaction can often be seen, especially in the subchondral bone marrow underlying the specific insertion of the ligament or tendon. Both microscopy (Ball J., Ann Rheum Dis. 1971 May; 30(3):213-23) and MRI images (McConagle D. et al., Arthritis Rheum 1998; 41(4):694-700) have demonstrated bone edema and infiltration of some T cells and macrophages. This potentially leads to local bone erosion, either in the subchondral bone (Fassbender, H. G., Pathologie Rheumatischer Erkrankungen, Springer Berlin, 1975) or at the insertion itself (Ball J., Ann Rheum Dis. 1971; 30(3):213-23). Some osteoclasts have been recognized in the subchondral bone marrow (Laloux L. Ann Rheum Dis. 2001; 60(4):316-21). However, these immune reactions are shortlived since they have only scarcely been documented. In a second phase, at least partly overlapping with the first phase, subchondral bone remodeling becomes apparent with the appearance of woven bone. At the outer side of the cortex, mesenchymal cell proliferation is striking, followed by differentiation into osteoblasts (recapitulating the embryological process of membranous ossification) or into proliferating chondrocytes, subsequently becoming hypertrophic chondrocytes and ultimately being replaced by osteoblasts (mimicking the embryological process of endochondral ossification). The proliferating and differentiating cells seem to use the existing fiber structures as scaffolds for new cartilage and bone formation. Membranous ossification is mostly seen under the periost, endochondral ossification at the insertions of tendons and ligaments. Ultimately two enthesitis/ossification processes at both ends of the joint meet, resulting in joint ankylosis. This phenomenon can be seen at all sites involved in SpA: synovial joints e.g. interphalangeal joints, zygoapophyseal joints, cartilaginous joints e.g. discovertebral junction, syndesmoses e.g. upper part of the sacroiliacal joints and extra-articular enthesis e.g. insertion of the Achilles tendon. In a last phase, also potentially overlapping with the other phases, complete joint ankylosis can occur, including fusion of the articular cartilages by endochondral bone formation. These pathological processess can ultimately result in a complete ossification of the intervertebral joints (immobile "bamboo spine" in AS), complete fusion of the sacroiliacal joints, interphalangeal joint ankylosis (often seen in PsA) and painful bony spurs at the tendon insertions (e.g. Achilles tendon).

Although many rheumatic diseases are associated with new bone formation (e.g. osteoarthritis and Diffuse Idiopathic Skeletal Hyperostosis), the specific association with inflammation and with the enthesial structures guiding the ossification process, delineates SpA bone formation as a clearly distinct entity. As stated above, the process of enthesitis and enthesial ankylosis not only causes significant pain and morbidity, but also impairs the functional capacities of the skeleton and leads to progressive disability. Although synovitis is frequent in SpA, causing significant problems for the patients, it is probably a secondary phenomenon caused by preceeding enthesitis.

"BMP-2" as used herein does not refer to BMP-2 A and B, a nomenclature used in the past to indicate BMP-2 and BMP-4, respectively. In the description hereafter, BMP-2 and BMP-4 nomenclature will be applied.

The term "Antibody" as used herein refers to IgG, IgM, IgD, IgA and IgG antibody. The definition includes polyclonal antibodies. This term refers to whole antibodies or fragments of the antibodies comprising the antigen-binding domain of the anti-BMP product antibodies e.g. antibodies without the Fc portion, single chain antibodies, fragments consisting of essentially only the variable, antigen-binding domain of the antibody, etc.

The term "BMP signaling pathway" as used herein, refers to the complex system of BMP-receptor interactions and responses thereof, mainly involving the Alk-2, Alk-3 and Alk-6 receptors.

The terms "inhibitor of BMP" or "BMP inhibitor" as used herein refers to an agent directly or indirectly neutralizing the activity of BMP, such as an agent interfering with BMP synthesis, formation, transcription, translation, receptor binding and/or receptor binding mediated signal transduction or with a BMP related pathway.

For purposes of the present invention an "antagonist of BMP" or "BMP antagonist" is an agent that binds with a BMP molecule (=ligand of BMP), such as but not limited to BMP2, BMP6 or BMP7, to form a complex wherein the BMP activity is neutralized, e.g. by preventing or inhibiting the binding of the BMP molecule by BMP receptors on target cell surfaces, or an agent that binds the BMP receptors (=ligand of BMP receptor), which results in suppression, prevention, reduction, or inhibition of BMP signal transduction.

Inhibitors or antagonists of BMP can be specific for a certain BMP or can have a lower degree of specificity, as such that the inhibitor or antagonist interacts with the activity of multiple BMPs.

With the term "treating" or "minimizing" SpA or SpA enthesitis for the purposes of this invention, it is understood that SpA or SpA enthesitis can be decreased for at least 20%, 30%, 40%, 50%, 60%, 70%, 80%, 90% or even 100%. SpA enthesitis can be measured as described herein further in the examples. For mice a standardised clinical protocol can be applied, while in human clinical standardised respons criteria as wel as radiological data can be used (Clegg, D. O. et al. Arthritis Rheum 1996; 39: 2013-2020; Braun, J. et al. Ann Rheum Dis 2002; 61 (Suppl 3): iii19-iii23; Van der Heijde, D. et al. Ann Rheum Dis 2002, 61 (Suppl 3): iii24-iii32; Braun, J. et al. Ann Rheum Dis 2002; 61 (Suppl 3): iii61-iii67). The term "neutralizing" or "inhibiting" the activity of BMP refers to an inhibition of at least 20%, 30%, 40%, 50%, 60%, 70%, 80%, 90% or even 100%. The activity of a BMP can be measured as described herein further in the examples.

The term "medicament to prevent or to treat" relates to a composition comprising molecules as described below and a pharmaceutically acceptable carrier or excipient (both terms can be used interchangeably) to prevent or to treat a disease as indicated above, the active ingredient preferably being in a concentration range of about 0 to 100% by weight.

The term "pharmaceutically acceptable carrier" as used herein means any material or substance with which the active ingredient is formulated in order to facilitate its application or dissemination to the locus to be treated, for instance by dissolving, dispersing or diffusing the said composition, and/or to facilitate its storage, transport or handling without impairing its effectiveness. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, suspensions, ointments, creams, tablets, pellets or powders.

In the present invention it is shown that Bone Morphogenetic Proteins, such as BMP-2, BMP-6 and BMP-7 are involved in the pathological development of ankylosing enthesitis, as seen in Spondyloarthropathies. In first instance it is shown that proinflamatory cytokines such as IL-1 and TNF-α induce BMP-2 and -6 expression in mesenchymal cells in vitro. This demostrates that mesenchymal cells, either from the synovium, the articular cartilage or the periost, can respond to an inflammatory stimulus, as seen in the first phase of the pathological sequence of SpA enthesitis, by selectively upregulating specific BMPs. The Spontaneous Arthritis in aging male DBA/1 mice can be considered as a model of Spondyloarthropathy. The mice develop namely a spontaneously occurring joint disease in an inbred strain and it is characerized by Ankylosing enthesitis. The present invention shows that specific BMPs are expressed in pathological enthesial chondro- and osteogenesis in aging male DBA/1 mice. Furthermore, the invention surprisingly shows that the use of inhibitors of BMPs significantly improves Spontaneous Arthritis in DBA/1 mice. Injections of Noggin, an antagonist of BMP, and overexpression of Noggin through injections of mouse Noggin cDNA in DBA/1 mice, efficiently inhibited Spontaneous Arthritis in aging male DBA/1 mice.

Therefore, the present invention realtes to the use of inhibitors of BMP for the treatment or prevention of SpA or SpA enthesitis in a mammal. In certain prefered embodiments, the present invention realtes to the use of inhibitors of BMP for the treatment or prevention of SpA or SpA enthesitis in a human. The BMP inhibitors may be administered systemically or locally with the appropriate pharmaceutical carrier. In a prefered embodiment the invention refers to the use of BMP inhibitors or a mixture thereof for the manufacture of a medicament for preventing, minimising and/or treating SpA or SpA enthesitis, comprising administering to a mammal a therapeutically effective amount of said agent.

In a certain embodiment, SpA or SpA enthesitis can be treated or prevented by modulating the BMP signaling pathway. In a prefered embodiment, said modulation of the BMP signaling pathway is induced by a BMP inhibitor or a mixture of different BMP inhibitors.

In a certain embodiment the present invention involves a method of treating or preventing SpA in a subject by administrating an antagonist of a BMP and BMP related protein e.g. BMP-2, BMP-6 and BMP-7. In a prefered embodiment, the present invention involves a method of treating or preventing SpA enthesitis in a subject by administering an antagonist of a BMP and BMP related protein e.g. BMP-2, BMP-6 and BMP-7. The antagonist can be a protein such as for example Noggin, Chordin, Follistatin, Gremlins, Fetuin, Cerberus and MGP (matrix Gla protein). The BMP antagonist can be from any mammalian source, homologous or heterologous to the species from which the epidermal basal(s) derive, or from an avian source. For example, bovine Fetuin can be useful and conveniently obtained, but other forms including human, porcine, ovine, equine, or avian forms, such as chicken, turkey or duck Fetuin can also be used. BMP antagonists, such as Noggin, Chordin, Follistatin, and Gremlin are also available to the skilled artisan. (E.g., Valenzuela et al., U.S. Pat. No. 5,843,775; Harland et al., U.S. Pat. No. 5,670,481; Ling et al., U.S. Pat. No. 5,041,538; Ling et al., U.S. Pat. No. 5,182,375; De Robertis et al., U.S. Pat. No. 5,679,783; LaVallie et al., U.S. Pat. No. 5,846,770; LaVallie et al., U.S. Pat. No. 5,986,056; R. Merino et al., Development 1999; 126(23):5515-5522; D. Sela-Donnenfeld and C. Kalcheim, Development 1999; 126 (21):4749-62). Alternatively, a synthetic or recombinant analog of a naturally occurring BMP antagonist or a variant or derivatives of a BMP antagonists are also useful in practicing the method. The synthesis of analogs of an antagonizing protein or peptides derived from an antagonizing protein or modifications thereof are known to a person skilled in the art.

The present invention provides furthermore a method to minimise, prevent or ameliorate SpA by administrating an antagonist to BMP-2, BMP-6 or BMP-7 such as an antibody, a soluble receptor or an oligonucleotide (aptamer strategy). In another embodiment of the invention SpA is treated by using cellular therapies using transformed or transduced cells expressing an antagonist of a BMP protein, or related protein, such as BMP-2, BMP-6 and BMP-7.

A preferred embodiment of the invention is treating or preventing SpA enthesitis by administrating an antagonist to BMP-2, BMP-6 and BMP-7 such as an antibody, a soluble receptor or an oligonucleotide (aptamer strategy). Yet another preferred embodiment is a method of treating enthesitis in SpA by using cellular therapies using transformed or transduced cells expressing an antagonist of BMP-2, BMP-6 and BMP-7.

In order to obtain oligonucleotides acting as an antagonist (aptamer strategy) of BMP, such as BMP-2, BMP-6 and BMP-7, techniques known to the skilled person in the art can be applied, such as but not restricted to the SELEX-strategy (Jäschke, A. et al., Synlett. 1999; 6: 825-833). Screening assays in this regard are known in the art, as described for example in PCT/US99/12001.

The present invention also provides for antibodies to a Bone Morphogenetic Protein such as BMP-2, BMP-6 and BMP-7 which are useful for treating or preventing SpA or for treating or preventing SpA enthesitis. Antibodies neutralizing the activity of BMP have been described (for example in Otsuka, -F. et al. Proc. Natl. Acad. Sci. U.S.A. 2002; 99(12): 8060-8065). Monoclonal antibodies against BMPs or related proteins can be produced by any technique which provides the production of antibody molecules by continuous cell lines in cultures such as the hybridoma technique originally developed by Kohler and Milstein (Kohler and Milstein Nature 1975, 256: 495-497), as well as the trioma technique, the human B-cell hybridoma technique (Kozbor et al., Immunology Today 1983, 4: 72), the EBV-hybridoma technique to produce human monoclonal antibodies (Cole et al. 1985, in "Monoclonal Antibodies and Cancer Therapy," Alan R. Liss, Inc. Pp 77-96) and the like, all are within the scope of the present invention.

The monoclonal antibodies against a BMP protein, or related protein, such as BMP-2, BMP-6 and BMP-7 for treatment or prevention of SpA or for treating or preventing SpA enthesitis may be human monoclonal antibodies or chimeric human-mouse (or other species) monoclonal antibodies or even from any other kind known in the art, such as coming from cammels or lamas. Human monoclonal antibodies may be made of any numerous techniques known in the art (e.g. Teng et al, Proc. Natl. Acad. Sci. U.S.A. 1983, 80: 7308-7312; Kozbor et al., Immunology Today 1983, 4: 72-79, Olsson et al, Meth. Enzymol. 1982, 92: 3-16). Chimeric antibody molecules may be prepared containing a mouse antigen-binding domain with human constant regions (Morrison et al, Proc. Natl. Acad. Sci. U.S.A. 1994, 81: 6851, Takeda et al. Nature 1985, 314: 452). Various procedures known in the art may be used for the production of polyclonal antibodies to epitopes of the BMP proteins such as the Bone Morphogenetic Proteins described herein. For the production of antibody, various host animals can be immunized by injection with a specific BMP protein or related protein, or a fragment or derivative thereof, including but not limited to rabbits, mice and rats. Various adjuvants may be used to increase the immunological response, depending on the host species, and including but not limited to Freund's (complete and incomplete), mineral gels such as aluminum hydroxide, surface active substances such as lysolecithin, pluronic polyosl, polyanions, peptides, oil emulsions, keyhole limpet hemocyanisn, dinitrophenols, and potentially useful human adjuvants such as BCG (Bacille Calmette-Guerin) and *Corynebacterium parvum.*

A molecular clone of an antibody to a selected BMP protein epitope or related protein epitope can be prepared by known techniques. Recombinant DNA methodology (see e.g. Maniatis et al., 1982, Molecular Cloning, A Laboratory Manual, Cold Spring Harbor Laboratory, New York) may be used to construct nucleic acid sequences which encode a monoclonal antibody molecule, or antigen binding region thereof.

The present invention provides for antibody molecules as well as fragments of such antibody molecules. Antibody fragments, which contain the idiotype of the molecule, can be generated by known techniques. For example, such fragments include but are not limited to the F(ab')2 fragment which can be produced by pepsin digestion of the antibody molecule, the Fab' fragments which can be generated by reducing the disulfide bridges of the F(ab')2 fragment and the Fab fragments which can be generated by treating the antibody molecule with papain and a reducing agent. Antibody molecules can be purified by known techniques, e.g. immunoabsorption or immunoaffinity chromatography, chromatographic methods such as HPLC (high performance liquid chromatography), or a combination thereof.

In the present invention small molecules, e.g. small organic molecules with a molecular mass <500 Da and other suitable molecules, can also function as antagonists of BMPs, such as BMP-2, BMP-6 and BMP-7, in order to ameliorate or prevent SpA or SpA enthesitis. Small molecules and other drug candidates can readily be obtained, for example, from combinatorial and natural product libraries and using methods known to the art to screen candidate molecules for their BMP antagonizing function. Screening assays in this regard are known in the art, as described for example in PCT/US99/12001. Furthermore, random peptide libraries, consisting of all possible combinations of amino acids, attached to a solid phase or in solution, may also be used to identify peptides that act as antagonists of BMPs, such as BMP-2, BMP-6 and BMP-7.

Suitable BMP antagonists can also be developed by known drug design methods, e.g. using structural analysis of the BMPs employing methods established in the art, for example, using X-ray crystallography to analyze the structure of the complex formed by BMP and one of its known inhibitors (see for example Sielecki, A. R. et al. Science 1989; 243:1346-51; Dhanaraj, V. et al. Nature 1992; 357 (6377):466-72) and/or by modifying known BMP antagonists i.e. "lead compounds," to obtain more potent inhibitors and compounds for different modes of administration (i.e. oral vs. intravenous).

The present invention also provides a method of treating or preventing SpA or SpA enthesitis by using agents modulating expression of protein levels of morphogenetic proteins, including BMPs, CDMPs (Cartilage-derived morphogenetic protein), Gdfs (Growth/Differentiation factors) or members of the TGFbeta superfamily.

Inhibition of expression of a BMP such as BMP-2, BMP-6 and BMP-7 can be desirable to ameliorate or prevent SpA or SpA enthesitis. Where inhibition of expression of a BMP such as BMP-2, BMP-6 and BMP-7 is desirable to ameliorate or prevent SpA or SpA enthesitis, inhibitory nucleic acid sequences that interfere with expression of BMP such as BMP-2, BMP-6 and BMP-7 at the transcriptional or translational level can also be used. The strategy called antisense, antigene or RNA-interference can be applied. These approaches utilise, for example, antisense nucleic acids, ribozymes, triplex agents or siRNAs to block transcription or translation of a BMP such as BMP-2, BMP-6 and BMP-7 mRNA or DNA or of a specific mRNA or DNA of a BMP such as BMP-2, BMP-6 and BMP-7, either by masking that mRNA with an antisense nucleic acid or DNA with a triplex agent, by cleaving the nucleotide sequence with a ribozyme or by destruction of the mRNA through a complex mechanism involved in RNA-interference.

Antisense nucleic acids are DNA or RNA molecules or nucleic acid analogs (e.g. hexitol nucleic acids, Peptide nucleic acids) that are complementary to at least a portion of a specific mRNA molecule (Weintraub Scientific American 1990; 262:40). In the cell, the antisense nucleic acids hybridise to the corresponding mRNA, forming a double-stranded molecule. The antisense nucleic acids interfere with the translation of the mRNA, since the cell will not translate a mRNA that is double-stranded. Antisense oligomers of about 15 nucleotides are preferred, since they are easily synthesised and are less likely to cause problems than larger molecules when introduced into the target cell which produces a BMP such as BMP-2, BMP-6 and BMP-7. Also nucleic acids or analogs, complementary to the translation initiation site, e.g. between −10 or +10 regions of the BMP nucleotide sequence, are preferred.

The potency of antisense oligonucleotides for inhibiting BMP may be enhanced using various methods including addition of polylysine, encapsulation into liposomes (antibody targeted, cationic acid, Sendai virus derived, etc.) or into nanoparticels in order to deliver the oligonucleotides into cells. Other techniques for enhancing the antisense capacity of oligonucleotides exist, such as the conjugation of the antisense oligonucleotides for example to "cell penetrating peptides" (Manoharan, M. Antisense Nucleic Acid Drug Dev. 2002; 12(2): 103-128/Juliano, R.-L. Curr. Opin. Mol. Ther. 2000; 2(3): 297-303).

Use of for example an oligonucleotide or a PNA (Peptide nucleic acid) to stall transcription is known as the antigene strategy (e.g. triplex formation) In the case of oligonucleotides, the oligomer winds around double-helical DNA (major groove), forming a three-stranded helix. Therefore, these antigene compounds can be designed to recognise a unique site on a chosen gene and block transcription of that gene in vivo. (Maher et al. Antisense Res. and Dev. 1991; 1:227; Helene, C. Anticancer Drug Design 1991; 6:569/ Casey, B. P. et al. Prog. Nucleic Acid Res. Mol. Biol. 2001; 67: 163-192/Pooga, M. et al. Biomol. Eng. 2001; 17(6): 183-192/Nielsen, P. E. Pharmacol. Toxicol. 2000; 86(1): 3-7). Antigene oligonucleotides as wel as PNAs are easily synthesised by the man skilled in the art and are even commercially available.

Ribozymes are molecules possessing the ability to specifically cleave other single stranded RNA in a manner analogous to DNA restriction endonucleases. Through the modification of nucleotide sequences which encode these RNAs, it is possible to engineer molecules that recognise specific nucleotide sequences in an RNA molecule and cleave it (Cech J. Amer. Med. Assn. 1988; 260:3030). A major advantage of this approach is that, because they are sequence-specific, only mRNAs with particular sequences are inactivated.

There are two basic types of ribozymes namely, tetrahymena-type (Hasselhoff (1988) Nature 334:585) and "hammerhead"-type. Tetrahymena-type ribozymes recognise sequences which are four bases in length, while "hammerhead"-type ribozymes recognise base sequences 11-18 bases in length. The longer the recognition sequence, the greater the likelihood that the sequence will occur exclusively in the target mRNA species. Consequently, hammerhead-type ribozymes are preferable to tetrahymena-type ribozymes for inactivating a specific mRNA species and 18-based recognition sequences are preferable to shorter recognition sequences.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for predicted structural features such assecondary structure that may render the oligonucleotide sequence unsuitable. The suitability of candidate targets may also be evaluated by testing their accessibility to hybridization with complementary oligonucleotides, using ribonuclease protection assays.

RNA-interference involves the insertion of small pieces of double stranded (ds) and even single stranded RNA into a cell. If the dsRNA corresponds with a gene in the cell, it will promote the destruction of mRNA produced by that gene, thereby preventing its expression. The technique has been shown to work on a variety of genes, even in human cells and in vivo. For example small interfering RNAs (siRNA), short-hairpin RNAs (shRNA) or vectors expressing such nucleic acids can be applied in the RNA-interference strategy in order to inhibit the translation of BMP-mRNA.

Anti-sense RNA, DNA molecules and analogs, ribozymes, antigene compounds or nucleic acids for RNA interference of the invention may be prepared by any method known in the art for the synthesis of nucleic acid molecules. These include techniques for chemically synthesizing oligonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Suppression function of a BMP such as BMP-2, BMP-6 and BMP-7 can also be achieved through administration of variant polypeptide (dominant negative variant form) of BMP such as BMP-2, BMP-6 and BMP-7, or a nucleotide sequence encoding variant polypeptide of that BMP such as BMP-2, BMP-6 and BMP-7. Administering a BMP such as BMP-2, BMP-6 and BMP-7 variant polypeptide or a nucleotide sequence encoding such polypeptide, the variant will compete with wild-type BMP such as BMP-2, BMP-6 and BMP-7 for binding to its receptor.

Another aspect of the present invention is the use of gene transfer, including gene therapy, to deliver above mentioned molecules inhibiting BMP. Gene therapy means the treatment by the delivery of therapeutic nucleic acids to patient's cells. This is extensively reviewed in Lever and Goodfellow 1995; Br. Med Bull.,51, 1-242; Culver1995; Ledley, F. D. 1995. Hum. Gene Ther. 6, 1129. By gene transfer, a nucleic acid encoding a BMP-antagonising agent, such as Noggin, is introduced into cells in a subject to express the BMP-antagonist and inhibit the BMP function. To achieve gene therapy there must be a method of delivering genes to the patient's cells and additional methods to ensure the effective production of any therapeutic genes. There are two general approaches to achieve gene delivery; these are non-viral delivery and virus-mediated gene delivery.

In one embodiment of the invention, nucleic acid encoding a BMP-inhibitor is introduced in a subject in order to express the BMP-inhibitor and prevent or treat SpA or SpA enthesitis. For gene transfer, the key steps are 1) to select the mode of delivery, e.g. a proper vector for delivery of the inhibitor genes to the subject, 2) administer the nucleic acid to the subject; and 3) achieve appropriate expression of the transferred gene for satisfactory durations. Methods for gene transfer are known in the art. The method described below are merely for purposes of illustration and are typical of those that can be used to practice the invention. However, other procedures may also be employed, as is understood in the art. Most of the techniques to construct delivery vehicles such as vectors and the like are widely practiced in the art, and most practitioners are familiar with the standard resource materials which describe specific conditions, reagents and procedures. The following paragraphs may serve as a guideline.

Techniques for nucleic acid manipulation are well known. (See, e.g. Annual Rev. of Biochem. 1992; 61:131-156). Reagents useful in applying such techniques, such as restriction enzymes and the like, are widely known in the art and commercially available from a number of vendors. Large amounts of the nucleic acid sequences encoding the BMP-inhibitors may be obtained using well-established molecular biology procedures such as molecular cloning and replication of the vector or plasmid carrying the sequences in a suitable host cell. Either complete gene sequences or partial sequences encoding the desired BMP-inhibitors can be employed. The nucleic acid sequences encoding the BMP-inhibitors can also be produced in part or in total by chemical synthesis, e.g. by the phosphoramidite method described by Beaucage and Carruthers (Tetra Letts. 1981; 22:1859-1862) or the triester method (Matteucci et al., J. Am. Chem. Soc. 1981; 103:3185) and may be performed on commercial automated oligonucleotide synthesizers. A double-stranded fragment may be obtained from the single-stranded product of chemical synthesis either by synthesizing the complementary strand and annealing the strand together under appropriate conditions, or by synthesizing the complementary strand using DNA polymerase with an appropriate primer sequence.

The natural or synthetic nucleic acid coding for the inhibitors for expression in a subject may be incorporated into vectors capable of introduction into and replication in the subject. In general, nucleic acid encoding the selected inhibitor molecules is inserted, using standard recombinant techniques, into a vector containing appropriate transcription and translation control sequences, including initiation sequences operably linked to the gene sequence to result in expression of the recombinant genes in the recipient host cells. "Operably linked" means that the components are in a physical and functional relationship permitting them to function in their intended manner. The selected nucleic acid sequences are inserted into a single vector or separate vectors. More than one gene encoding a selected inhibitor, or portion thereof, may be inserted into a single vector or into separate vectors for introduction into the host cells. Alternatively, these sequences can be administered as naked nucleic acid sequences or as part of a complex with other molecules, e.g. liposomes.

A variety of expression vectors and gene transfer methods useful for obtaining expression of a BMP-inhibitor in recipient cells are well known in the art, and can be constructed using standard ligation and restriction techniques (see, for example, Sambrook et al., Molecular Cloning: A Laboratory Manual, Cold Spring Harbor Laboratory Press, 1989; Maniatis et al., Molecular Cloning: A Laboratory Manual, Cold Spring Harbor, N.Y. (1982), Kriegler, Gene Transfer and Expression: A Laboratory Manual (W. H. Freeman and Co., New York, N.Y. 1990) and Wu, Methods in Enzymol. (Academic Press, New York, N.Y. 1993), each of which is incorporated by reference herein). Suitable vectors may be plasmid or viral vectors (Kaufman, in Gene Expression Technology, Goeddel (Ed.) (1991)) including baculoviruses, adenoviruses, poxviruses (Moss, Current Opin. Biotech. 3:518-522 (1993)), retrotransposon vectors (Cook et al., Bio/Technology 1991; 9:748-751; Chakraborty et al. FASEB J. 1993; 7:971-977) adeno-associated viruses (AAV) (Yei et al., Gene Therapy 1994; 1:192-200; Smith et al., Nat. Genet. 1993; 5:397-402), herpes virus and retrovirus vectors (Price et al., Proc. Natl. Acad. Sci. USA 1987; 84:156-160; Naviaux and Verma, Current Opinion in Biotechnol. 1992; 3:540-547; Hodgson and Chakraborty, Curr. Opin. Thera. Patients 1993; 3:223-235) such as the MMLV based replication incompetent vector pMV-7 (Kirschmeier et al., DNA 1988; 7:219-225), as well as human and yeast artificial chromosomes (HACs and YACs) (Huxley, Gene Therapy 1994; 1:7-12; Huxley et al., Bio/Technology 1994; 12:586-590). Plasmid expression vectors include plasmids including pBR322, pUC or Bluescripttm (Stratagene, San Diego, Calif.).

Vectors containing the nucleic acid encoding the inhibitory agents are preferably recombinant expression vectors in which high levels of gene expression may occur, and which contain appropriate regulatory sequences for transcription and translation of the inserted nucleic acid sequence. Regulatory sequences refer to those sequences normally associated (e.g. within 50 kb) of the coding region of a locus which affect the expression of the gene (including transcription, translation, splicing, stability or the like, of the messenger RNA). A transcriptional regulatory region encompasses all the elements necessary for transcription, including the promoter sequence, enhancer sequence and transcription factor binding sites. Regulatory sequences also include, inter alia, splice sites and polyadenylation sites. An internal ribosome entry site (IRES) sequence may be placed between recombinant coding sequences to permit expression of more than one coding sequence with a single promoter.

Transcriptional control regions include: the SV40 early promoter region, the cytomegalovirus (CMV) promoter (human CMV IE94 promoter region (Boshart et al., Cell 1985; 41:521-530); the promoter contained in the 3' long terminal repeat of Rous Sarcoma Virus or other retroviruses; the herpes thymidine kinase promoter; the regulatory sequences of the methallothionein gene; regions from the human IL-2 gene (Fujita et al., Cell 1986; 46:401-407); regions from the human IFN gene (Ciccarone et al., J. Immunol. 1990; 144:725-730); regions from the human IFN gene (Shoemaker et al., Proc. Natl. Acad. Sci. USA 1990; 87:9650-9654); regions from the human IL-4 gene (Arai et al., J. Immunol. 1989; 142:274-282); regions from the human lymphotoxin gene (Nedwin et al., Nucl. Acids. Res. 1985; 13:6361-6373); regions from the human granulocyte-macrophage CSF gene (GM-CSF) (Miyatake et al., EMBO J. 1985; 4:2561-2568) and others. When viral vectors are used, recombinant-coding sequences may be positioned in the vector so that their expression is regulated by regulatory sequences such as promoters naturally residing in the viral vector.

Operational elements for obtaining expression may include leader sequences, termination codons and other sequences needed or preferred for the appropriate transcription and translation of the inserted nucleic acid sequences. Secretion signals may also be included whether from the native inhibitor or from other secreted polypeptides, which permit the molecule to enter cell membranes and attain a functional conformation. It will be understood by one skilled in the art that the correction type and combination of expression control elements depends on the recipient host cells chosen to express the molecules ex vivo. The expression vector should contain additional elements needed for the transfer and subsequent replication of the expression vector containing the inserted nucleic acid sequences in the host cells. Examples of such elements include, but are not limited to, origins of replication and selectable markers. Additionally, elements such as enhancer sequences, for example CMV enhancer sequences, may be used to increase the level of therapeutic gene expression (Armelor. Proc. Natl. Acad. Sci. USA 1973; 70:2702).

The vector may contain at least one positive marker that enables the selection of cells carrying the inserted nucleic acids. The selectable molecule may be a gene which, upon introduction into the host cell, expresses a dominant phenotype permitting positive selection of cells carrying the gene ex vivo. Genes of this type are known in the art and include, for example, drug resistance genes such as hygromycin-B phosphotransferase (hph) which confers resistance to the antibiotic G418; the aminoglycoside phosphotransferase gene (neo or aph) from Tn5 which codes for resistance to the antibiotic G418; the dihydrofolate reductase (DHRF) gene; the adenosine deaminase gene (ADA) and the multi-drug resistance (MDR) gene.

Recombinant viral vectors are introduced into host cells using standard techniques. Infection techniques have been developed which use recombinant infectious virus particles for gene delivery into cells. Viral vectors used in this way include vectors derived from simian virus 40 (SV40; Karlsson et al., Proc. Natl. Acad. Sci. USA 1985; 82:158); adenoviruses (Karlsson et al., EMBO J. 1986; 5:2377); vaccinia virus (Moss et al., Vaccine 1988; 6:161-3); and retroviruses (Coffin, in Weiss et al. (Eds.), RNA Tumor Viruses, $2^{nd}$ Ed., Vol. 2, Cold Spring Laboratory, N.Y., pp. 17-71 (1985)). Nonreplicating viral vectors can be produced in packaging cell lines which produce virus particles which are infectious but replication defective, rendering them useful vectors for introduction of nucleic acid into a cell lacking complementary genetic information enabling encapsidation (Mann et al., Cell 1983; 33:153; Miller and Buttimore, Mol. Cell. Biol. 6:2895 (PA317, ATCC CRL9078)). Packaging cell lines which contain amphotrophic packaging genes able to transduce cells of human and other species origin are preferred. Vectors containing the inserted inhibitor genes or coding sequences are introduced into host cell using standard methods of transfection including electroporation, liposomal preparations, Ca-PH-DNA gels, DEAE-dextran, nucleic acid particle "guns" and other suitable methods.

In additional to various vectors including viral and non-viral vectors, other delivery systems may be used including, but not limited to, microinjection (DePamphilis et al., Bio-Technique 1988; 6:662-680); liposomal mediated transfection (Feigner et al., Proc. Natl. Acad. Sci. USA 1987; 84:7413-7417; Feigner and Holm, Focus 1989; 11:21-25 and Feigner et al., Proc. West. Pharmacol. Soc. 1989; 32:115-121); use of naked or particle mediated DNA transfer and other methods known in the art. Recently, cationic liposomes have been used to enhance transfection (Feigner et al., Nature 1991; 349:351; Zhu et al., Science 1993; 261: 209).

Suitable host cells for gene transfer consist of vertebrate cells such as fibroblasts, keratinocytes, muscle cells, mesangial cells (see, Kitamura et al., Kidney Int. 1995; 48:1747-1757), and any other suitable host cell including so-called universal host cells, i.e. cells obtained from a different donor than the recipient subject but genetically modified to inhibit rejection by the subject. Autologous cells are preferred, but heterologous cells are encompassed within the scope of the invention. Expression of the selected inhibitor genes after introduction into the host cells is confirmed by assaying for the ability of the supernatant to inhibit the activity of BMP.

In a specific embodiment it should be clear that the preventive and therapeutic method of the present invention against SpA or SpA enthesitis can also be used in combination with any other therapy known in the art for SpA or SpA enthesitis. A combination of the presented therapeutic methods described herein are therefore also possible.

Pursuant to the method of the present invention, at least one inhibitor of BMP such as BMP-2, BMP-6 and BMP-7 is maintained in an effective concentration at the site of potential SpA or SpA enthesitis for a period of time sufficient to be effective. A mixture of different inhibitors of BMP can also be applied.

The inhibitor of BMP such as BMP-2, BMP-6 and BMP-7 may be administered directly in a suitable vehicle, for example phosphate buffered saline. In another embodiment at least one specific inhibitor of BMP such as BMP-2, BMP-6 and BMP-7 is administered in a drug-delivery system which enables the maintenance of requisite concentrations of an inhibitor of BMP such as BMP-2, BMP-6 and BMP-7 for a period of time sufficient for ameliorating SpA or enthesitis in SpA in a single dose delivery.

To optimise the pharmacokinetic lifetime of the compounds of present invention they can be administered in conjunction with a suitable delivery vehicle (e.g., microcapsules, microspheres, biodegradable polymer films, lipid-based delivery systems such as liposomes and lipid foams, viscous instillates and absorbable mechanical barriers) useful for maintaining local concentrations of the compound at the injury site or the potential site of SpA at an effective level.

The present invention provides a topically applicable pharmaceutical composition to prevent or to ameliorate SpA or SpA enthesitis, comprising a therapeutically effective amount of sparingly soluble inhibitor of BMP such as BMP-2, BMP-6 and BMP-7 in which dissolves at a desired rate in a biofluid such that said composition is capable of delivering said for a period of days or weeks when applied to a site of potential SpA, the rate of dissolution in use being due to the sparing solubility of the inhibitor of Bone Morphogenetic Protein BMP such as BMP-2, BMP-6 and BMP-7. Such form of inhibitor may be of relative low solubility in biofluids such as plasma, interstitial or peritoneal, the rate of dissolution being selected so that the enzyme will dissolve in the biological fluid over a period sufficient to prevent or to ameliorate SpA or SpA enthesitis.

This can enable a single topical application. This inhibitor of inhibitor of BMP such as BMP-2, BMP-6 and BMP-7 of relative low solubility in biofluids can be at solid state, optionally a powder at the time of application at the site of potential SpA, or it can be submitted in a semi-solid pharmaceutical formulation with suitable thickening agent, a solid dispersion ingredients wherein the inhibitor is dispersed in the solid state (microparticular, even molecular) in an inert solid vehicle or it can be in the form solution in an appropriate solvent. The race of dissolution is selected so that the inhibitor of BMP such as BMP-2, BMP-6 and BMP-7 will mix in the biological fluid over a period sufficient to prevent SpA. To reduce the appearance at undesirable locations the inhibitor of BMP such as BMP-2, BMP-6 and BMP-7 may be combined with an inert adherence enhancing vehicles or mixture thereof such as long chain hydrocarbons or vegetable oils and waxes composed of mixtures of saturated and unsaturated fatty acid glycerides or mixtures of modified saturated and unsaturated fatty acid glycerides.

Such vehicles or carriers include, but are not limited to, semisolid vehicles such as petrolatum jelly or semi-synthetic glycerides, polyhydroxy solvents, such as glycerol, long chain hydrocarbons, bioerodable polymers or liposomes. Included within bioerodable polymers are low molecular weight polymers which can be formulated in semi-solid form. Such formulated semisolid polymers include poly (esters), polyamides, poly(amino acids), polyacetals, polyanhydrides, poly(ortho ester)s and polysaccharides such as the natural carbohydrate consisting of alternating β-D-glucuronic acid and 2-acetamido-2-deoxy-β-D-glucose known as hyaluronic acid.

Embodiments of the present invention may enable one to achieve one or more of the following objects: to provide a composition preventing or ameliorating SpA or enthesitis in SpA; by providing a composition that is suitable to deliver a pharmaceutical effective amount of inhibitor of BMP such as BMP-2, BMP-6 and BMP-7. The concentration of this inhibitor which can be administered may be varied over a fairly broad range, the concentration being limited by efficacy at the lower end and complications at the upper end.

In a certain embodiment of the invention the above described molecules can be used to manufacture a medicament to prevent or to treat SpA or SpA enthesitis.

Suitable pharmaceutical carriers for use in said pharmaceutical compositions and their formulation are well known to those skilled in the art, and there is no particular restriction to their selection within the present invention. Suitable carriers or excipients known to the skilled man are saline, Ringer's solution, dextrose solution, Hank's solution, fixed oils, ethyl oleate, 5% dextrose in saline, substances that enhance isotonicity (such as sugars or sodium chloride) and chemical stability, buffers and preservatives. Other suitable carriers include any carrier that does not itself induce the production of antibodies harmful to the individual receiving the composition such as proteins, polysaccharides, polylactic acids, polyglycolic acids, polymeric amino acids and amino acid copolymers. They may also include additives such as wetting agents, dispersing agents, stickers, adhesives, emulsifying agents, solvents, coatings, antibacterial and antifungal agents (for example phenol, sorbic acid, chlorobutanol) and the like, provided the same are consistent with pharmaceutical practice, i.e. carriers and additives which do not create permanent damage to mammals. The pharmaceutical compositions of the present invention may be prepared in any known manner, for instance by homogeneously mixing, coating and/or grinding the active ingredients, in a one-step or multi-steps procedure, with the selected carrier material and, where appropriate, the other additives such as surface-active agents may also be prepared by inicronisation, for instance in view to obtain them in the form of microspheres usually having a diameter of about 1 to 10 μm, namely for the manufacture of microcapsules for controlled or sustained release of the active ingredients.

Suitable surface-active agents to be used in the pharmaceutical compositions of the present invention are non-ionic, cationic and/or anionic materials having good emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher fatty acids (CIO-C22), e.g. the sodium or potassium salts of oleic or stearic acid, or of natural fatty acid mixtures obtainable form coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates are the sodium, calcium or alcanolamine salts of dodecylbenzene sulphonic acid or dibutyl-naphtalenesulphonic acid or a naphtalene-sulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanylphosphatidyl-choline, dipalmitoylphoshatidyl-choline and their mixtures.

Suitable non-ionic surfactants include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with poylypropylene glycol, ethylenediaminopolypropylene glycol containing 1 to 10 carbon atoms in the alkyl chain, which adducts contain 20 to 250 ethyleneglycol ether groups and/or 10 to 100 propyleneglycol ether groups. Such compounds usually contain from I to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxypolyethoxyethanol, polyethyleneglycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants include quaternary ammonium salts, preferably halides, having 4 hydrocarbon radicals optionally substituted with halo, phenyl, substituted phenyl or hydroxy; for instance quaternary ammonium salts containing as N-substituent at least one C8C22 alkyl radical (e.g. cetyl, lauryl, palmityl, myristyl, oleyl and the like) and, as further substituents, unsubstituted or halogenated lower alkyl, benzyl and/or hydroxy-lower alkyl radicals.

A more detailed description of surface-active agents suitable for this purpose may be found for instance in "McCutcheon's Detergents and Emulsifiers Annual" (MC Publishing Crop., Ridgewood, N.J., 1981), "Tensid-Taschenbucw', 2 d ed. (Hanser Verlag, Vienna, 1981) and "Encyclopaedia of Surfactants, (Chemical Publishing Co., New York, 1981).

Additional ingredients may be included in order to control the duration of action of the active ingredient in the composition. Control release compositions may thus be achieved by selecting appropriate polymer carriers such as for example polyesters, polyamino acids, polyvinyl pyrrolidone, ethylene-vinyl acetate copolymers, methylcellulose, carboxymethylcellulose, protamine sulfate and the like. The rate of drug release and duration of action may also be controlled by incorporating the active ingredient into particles, e.g. microcapsules, of a polymeric substance such as hydrogels, polylactic acid, hydroxymethylcellulose, polyniethyl methacrylate and the other above-described polymers.

Such methods include colloid drug delivery systems like liposomes, microspheres, microemulsions, nanoparticles, nanocapsules and so on. Depending on the route of administration, the pharmaceutical composition may require protective coatings. Pharmaceutical forms suitable for injectionable use include sterile aqueous solutions or dispersions and sterile powders for the extemporaneous preparation thereof. Typical carriers for this purpose therefore include biocompatible aqueous buffers, ethanol, glycerol, propylene glycol, polyethylene glycol and the like and mixtures thereof.

The BMP-inhibitor or "medicament" may be administered by any suitable method within the knowledge of the skilled man. Modes of administration of the inhibitors known in the art for therapeutic agents include parenteral, for example, intravenous (e.g. for antibody inhibitors), intraperitoneal, intramuscular, intradermal, and epidermal including subcutaneous and intradermal, oral (e.g. small molecule BMP antagonists), or applied to mucosal surfaces, e.g. by intranasal administration using inhalation of aerosol suspensions, and by implanting to muscle or other tissue in the subject (e.g. for gene transfer of nucleic acid expressing BMP inhibitors). Suppositories and topical, locally applied preparations are also contemplated.

In the present invention, the inhibitors are introduced in amounts sufficient to prevent, reduce or treat SpA or SpA enthesitis, depending on the administration route.

The most effective mode of administration and dosage regimen for the inhibitors or the "medicament" in the methods of the present invention depend on the severity of the SpA or SpA enthesitis, the subject's health, previous medical history, age, weight, height, sex and response to treatment and the judgment of the treating physician. Therefore, the amount of inhibitors to be administered, as well as the number and timing of subsequent administrations are determined by a medical professional conducting therapy based on the response of the individual subject. Initially, such parameters are readily determined by skilled practitioners using appropriate testing in animal models for safety and efficacy, and in human subjects during clinical trials of candidate therapeutic inhibitor formulations. Suitable animal models of SpA are known and incorporated herein. After administration, the efficacy of the therapy using the inhibitors is assessed by various methods including assessment of the clinical picture.

Materials and Methods

Recombinant Proteins, Antibodies and Cell Lines

Recombinant proteins were obtained from the following sources: recombinant human IL1β and recombinant human TNF-α from Biosource International (Nivelles, Belgium) and recombinant human IFN-γ from Boehringer Mannheim (Mannheim, Germany). Goat affinity purified polyclonal anti-human, -mouse, -rat BMP-6 antibody and blocking peptides were purchased from Santa Cruz Biotechnologies (Santa Cruz, Calif.). This antibody was raised against a peptide sequence from the amino-terminus of human BMP-6. Affinity purified polyclonal chicken anti-human BMP-2 and BMP-7 antibodies were a gift from Pfizer Central Research (Groton, Conn.). Anti-BMP-2 antibody was raised against peptide sequence Ac-REKRQAKHKARKRLKSSC-NH$_2$ (SEQ ID NO:1). BLAST protein analysis showed that this peptide is specific for BMIP-2 and is conserved cross-species (human, mouse, rat, *xenopus*). Anti-BMP-7 antibody was raised against peptide sequence Ac-TGSKQRSQNR-SKTPKNC-NH$_2$ (SEQ ID NO:2). This peptide sequence is specific for human BMP-7 as shown by BLAST protein analysis. The mouse and rat BMP-7 sequence shows 1 amino-acid difference (G in stead of S in position 3).

Patient Materials and Cell Isolation Techniques

Arthroscopy materials: Patients were treated at the Department of Rheumatology or the Department of Orthopedic Surgery, University Hospitals Leuven and gave written informed consent. The local Ethical Committee approved the procedure. All patients with inflammatory arthritis included in the study fulfilled either the revised American College of Rheumatology (ACR) (formerly, the American Rheumatism Association) criteria for RA (Arnett, F. C. et al. Arthritis Rheum. 1988; 31: 315-324) or the ESSG criteria for SpA (Dougados, M. et al. Arthritis Rheum. 1991; 34: 1218-1227). For a diagnosis of knee Osteoarthritis (OA), ACR criteria were used (Altman, R. et al. Arthritis Rheum. 1986; 29, 1039-1049). Other diagnoses for the control samples were made by combining clinical, radiological and arthroscopy data. Needle arthroscopy of the knee, with random synovial biopsies, was performed under sterile and standardized conditions.

FLS isolation: Two biopsies were washed twice in Hanks' balanced salt solution (HBSS; Life Technologies, Merelbeke, Belgium) supplemented with 2× antibiotic-antimycotic solution (100 U/ml penicillin, 100 μg/ml streptomycin and 0.25 μg/ml amfotericin B; Life Technologies). Cells were isolated using a previously described protocol (De Bari, C. et al. Arthritis Rheum. 2001; 44: 1928-1942). All tissue culture experiments were performed at 37° C. in a humidified atmosphere of 5% CO$_2$. The biopsies were digested overnight with 0.2% Type IV Collagenase (Life Technologies) in high-glucose Dulbecco's modified Eagle's medium (DMEM; Life Technologies) containing 10% fetal bovine serum (FBS; Bio-Whittaker, Verviers, Belgium) and 2× antibiotics (as above). Passage 0 (P0) cells from both biopsies were pooled and washed in DMEM-10% FBS and antibiotics (growth medium) twice and then resuspended in 3 ml growth medium and plated in 3 different wells of a 6-well tissue culture plate. Non-adherent cells were removed after 72 hours by changing growth medium.

After reaching confluence, cells were washed twice with Dulbecco's calcium and magnesium-free phosphate buffered saline (DPBS; Bio-Whittaker), harvested with trypsin-EDTA (0.25% trypsin, 1 mM EDTA; Life Technologies), and replated in a T75 flask. Further passaging was done with 1:3 dilutions. Growth medium was changed twice a week. All further experiments were performed between P4 en P9.

Periosteum-derived cells and chondrocytes: Periosteum and cartilage-derived cells from non-arthritic donors were a kind gift of Dr. C. De Bari and Dr. F. Dell'Accio. Cells were isolated using a similar procedure as for FLS.

Cytokine Stimulation Experiments

For cytokine stimulation experiments, harvested FLS were diluted 1:3 in growth medium and plated in 6-well tissue culture plates. At confluence, cells were either treated with ligands (IL-1β, TNF-α or IFN-γ) or carrier controls. In additional experiments, cells were plated on tissue culture slides and incubated at confluence with ligands as described above. In similar experiments periosteum-derived cells and chondrocytes at confluence in 6 well plates were used. At the indicated time points cells were processed for RNA extraction (see below).

Total RNA Extraction and Reverse Transcription Polymerase Chain Reaction (RT-PCR) Analysis.

Total RNA from stimulated cells or from fresh synovial biopsies was isolated using a commercially available kit (S.N.A.P.; Invitrogen, Merelbeke, Belgium) according to the manufacturer's instructions. Complementary DNA (cDNA) was obtained by RT of 1 to 2 µg total RNA (Thermoscript; Invitrogen) with oligo(dT)20 as primer. Conventional PCR was performed as previously described (de Bari, C. et al. Arthritis Rheum. 2001; 44: 1928-1942). Complementary DNA was mixed with 0.5 U Taq polymerase (Eurogentec, Seraing, Belgium), 0.2 mM dNTP, 0.5 µM specific primers and 1.5 mM MgCl2. Primer pairs were designed using Vector NTI software (Informax; North Bethesda, Md.). The sequences of some primers are shown in Table 1. All conventional PCR reactions were carried out in a Perkin Elmer Thermal Cycler 9600 (Applied Biosystems; Lennik, Belgium). After denaturation at 95° C. for 2 minutes, cycles were 10 seconds at 94° C., 10 seconds at 60° temperature, and 30 seconds at 72° C. Cycling was followed by a 10-minute elongation at 72° C. For BMP-7/Osteogenic Protein-1 (OP-1) PCR a two-step procedure using an annealing and elongation temperature of 68° C. for 45 seconds was used. PCR products were electrophoresed in 1.2% agarose gels in Tris-borate-EDTA electrophoresis buffer, stained with ethidium bromide, visualized by ultraviolet transillumination. For semi-quantitative analysis, cDNA was equalized for the expression of the housekeeping gene β-actin by densitometry using the Image Master software (Amersham Pharmacia Biotech, Roosendaal, The Netherlands).

TABLE 1

Primer sequences

| | | |
|---|---|---|
| OP1 S | GACATCACAGCCACCAGCAAC | (SEQ ID NO:3) |
| OP1 AS | GAAGTAGAGGACGGAGATGGG | (SEQ ID NO:4) |
| BMP6 S | CAGGAGCATCAGCACAGAGAC | (SEQ ID NO:5) |
| BMP6 AS | ATGTGTGCGTTGAGTGGGAAG | (SEQ ID NO:6) |
| BMP4 S | TTCCTGGTAACCGAATGCT | (SEQ ID NO:7) |
| BMP4 AS | GGGGCTTCATAACCTCATAA | (SEQ ID NO:8) |
| BMP2 S | CAGAGACCCACCCCCAGCA | (SEQ ID NO:9) |
| BMP2 AS | CTGTTTGTGTTTGGCTTGAC | (SEQ ID NO:10) |
| MMP3 S | TACCCAAGAGGCATCCACAC | (SEQ ID NO:11) |
| MMP3 AS | CGGCAAGATACAGATTCACG | (SEQ ID NO:12) |
| TGFB2 S | TCCAAAGATTTAACATCTCCAACC | (SEQ ID NO:13) |
| TGFB2 AS | TCCCACTGTTTTTTTTCCTAGTGG | (SEQ ID NO:14) |
| TGFB1 S | CAGAAATACAGCAACAATTCCTGG | (SEQ ID NO:15) |
| TGFB1 AS | TTGCAGTGTGTTATCCCTGCTGTC | (SEQ ID NO:16) |
| BACT S | TGACGGGGTCACCCACACTGTGCCCATCTA | (SEQ ID NO:17) |
| BACT AS | CTAGAAGCATTTGCGGTGGACGATGGAGGG | (SEQ ID NO:18) |

For real-time quantitative analysis, PCR was performed using the ABI Prism 7700 sequence detection system (Applied Biosystems). PCRs were run in a 12,5 µl mixture consisting of 3.5 mM MgCl$_2$, 200 µM of each dNTP, 0.5 µM specific primers, 0.025 U/µl Hot Goldstar enzyme, 1 µl of SYBR green dilution and 1× reaction buffer (all from Eurogentec). After initial activation of the Hot Goldstar enzyme (10 minutes at 95°), 40 cycles of 95° (10 seconds) denaturation and 60° (2 minutes) elongation were run. Non-specific amplification was detected by melting curve analysis using Applied Biosystems Dissociation Curves software. The identity of the PCR products was checked by DNA sequencing. For quantitative analysis, standard curves were generated using serial dilutions of cDNA. In preliminary experiments the validity of β-actin as a housekeeping gene was tested comparing it's expression levels to other housekeeping genes. For quantification, target gene expression levels were normalized for β-actin expression levels.

Spontaneous Arthritis in Aging Male DBA/1 Mice

General: Grouped aging male DBA/1 mice (Jackson laboratories) develop a form of arthritis with striking similarities to the SpA. Arthritis in aging male DBA/1 mice is a spontaneously occurring joint disease in an inbred strain without over immunological abnormalities. From 16 weeks onwards, the mice suffer from an asymmetrical arthritis mainly affecting the proximal interphalangeal hind paw joints and the ankles and is characterized by endochondral bone formation at the enthesis. (Nordling C. et al., Arthritis Rheum 1992; 35(6):17-22). The clinical picture is characterized by toe or paw swelling, redness, stiffness, loss of function and ultimately joint ankylosis. It is characterized by Ankylosing enthesitis and is therefore considered as a model of Spondyloarthropathy. The ankylosing enthesitis typically develops two to six weeks after grouped caging of DBA/1 males from different litters (>3 males per cage). Pathologically, a severe enthesitis is seen with an initial cell proliferation of mainly mesenchymal cells but also some macrophages. The enthesis subsequently shows neochondro- and osteogenesis with striking similarity to the pathology of the small joints in SpA. Enthesial neocartilage and bone formation are taking place in a way strongly reminiscent of embryological endochondral and membranous bone formation, probably depending on the specific site of the enthesial structure affected.

Clinical manifestations of SpAD: In 4 different experiments, 33 male DBA/1 mice were examined clinically. A complete microscopic analysis of forefeet and ankles from the hind paws (as described in the materials and methods section) was performed in 25 animals. In the first 3 experiments animals were killed 7 (age 21 weeks 10 mice) or 8 weeks (age 24 weeks 2 times 8 mice) after the first symptoms in the cohort developed. In one cohort (7 mice, aged 25 weeks) the animals were sacrificed 4 weeks after disease occurred in 2 animals. Disease incidence varied strongly from cohort to cohort.

Our clinical observations were largely similar to those reported (Corthay, A. et al. Arthritis Rheum. 2000; 43: 844-851). Joint swelling, joint stiffness as demonstrated by the loss of grip function on the cage grid and joint deformity were the major symptoms. We also noticed an abnormal position of the nail in affected animals suggesting specific involvement of the nail bed and/or distal phalanx. In total 66 paws were evaluated clinically. At the end of the observation period 26 out of 66 paws (39%) appeared normal. A score 1 (one toe affected) was awarded to 10 out of 66 paws (18%), a score 2 indicating that more than 1 toe is affected was found in 6 out of 33 paws (9%). Progressive disease as demonstrated by loss of grip function due to toe stiffness (score 3) was found in 11 out of 66 animals (17%). Ankle arthritis or persisting deformity of a toe was found in 13 out of 66 paws (20%). In addition nail involvement was noticed in 8 paws out of 66 (12%).

Pathological manifestations of SpAD: Three different manifestations of the disease were recognized on microscopic analysis. Besides typical signs of ankylosing enthesitis as previously reported by Corthay et al (2000) we also noticed dactylitis and onychoperiostitis. 4 different stages in the process of ankylosing enthesitis in SpAD have been distinguished. These different manifestations are most easily recognized in the PIP joints. In a first phase, a strong expansion of fibroblast-like cells is seen, probably through proliferation originating from the periost. Some of these cells were gradually differentiating from thin spindle shaped cells into more round-shaped cells reminiscent of chondroblasts. No inflammatory cells were recognized in this tissue except an occasional neutrophil.

The second phase is characterized by endochondral bone formation in the enthesis with differentiation of the chondroblastic cells into prehypertrophic-like and hypertrophic chondrocyte-like cells. The newly formed enthesial chondrocytes are effectively producing cartilaginous extra cellular matrix as could be demonstrated by both Safranin-O and Toluidine Blue staining.

In the third stage new bone formation becomes evident. The matrix surrounding the hypertrophic chondrocytes is invaded by small vessels. As in endochondral bone formation the matrix is gradually replaced by new bone. Sometimes, multinuclear giant cells are seen suggesting a role for osteo- or chondroclasts in AE.

Finally enthesial cartilage and bone formation on both sides of the joint is forming large enthesophyes that eventually fuse leading to partial or complete joint space bridging and ankylosis.

Experiments: For the experiments, male DBA/1 mice from different litters were caged together (>3 mice per cage) at the age of 10 to 12 weeks and checked twice weekly for clinical signs of arthritis. Mice were sacrificed between 18 and 30 weeks by cervical dislocation and hind paws were routinely processed for histology. The local Ethical Committee for Animal Experiments approved the procedures. After fixation (4% formaline) and decalcification (Decal, Clinipath) for 36 hours, paws were kept in methanol till parafin embedding. Sections were made on silanated slides.

Noggin Inhibition of BMP

In two different experiments Noggin treatment was used. Noggin cDNA in pcDNA 3.1 vector was a kind gift of R. Harland (Berkeley, Calif.). In these experiments, 300 or 30 µg of Noggin cDNA or empty vector were injected into the tibialis anterior muscle every 3 weeks switching between the right and left hind limb. Animals were checked for disease incidence and severity twice a week. Disease severity was quantified using the following score per hind paw: score 1=1 swollen joint or toe; score 2=>1 toe affected, score 3=toe stiffness, score 4=fixed deformity.

At the end of each experiment, mice hind paws were dissected, fixed in formalin for 16 hours, decalcified using Decal (Serva, Heidelberg, Germany) for 72 hours or 0.5 mM EDTA for 6 weeks, dehydrated and embedded in paraffin. Forefeet sections were cut in a transversal plane allowing analysis of all interphalangeal and metatarsophalangeal joints. Ankles were cut in a sagittal plane. A microscopic disease severity score was developed as follows: inflammation or proliferation of enthesial cells=1 point, cartilage formation=2 points, bone formation=3 points, joint space bridging=4 points. A cumulative score of all PIP, DIP and ankle joints from the hindpaws was made.

Immunohistochemistry and Immunofluorescence

Sections were extensively quenched with 0.3% $H_2O_2$ in $H_2O$. After washing 3 times in TBS for 5 minutes, blocking donkey serum (1:5 dilution in TBS) was added for 30 minutes at room temperature. Sections were subsequently incubated with primary chicken anti-human BMP-2 (5 µg/ml), BMP-7/OP-1 (10 µg/ml) antibody or chicken IgG (Jackson Immunoresearch Laboratories; West Grove, Pa.) at the same concentration (all diluted in TBS) at 4° C. overnight. After washing 3 times in TBS, a second blocking step was added and thereafter sections were incubated for 30 minutes at room temperature with a Horseradish Peroxidase conjugated rabbit anti-chicken antibody (1/100 dilution) (Jackson Immunoresearch Laboratories). For BMP-6 staining a polyclonal goat anti-BMP-6 antibody or goat IgG (Santa Cruz) were used (1/100 dilution). As a secondary antibody we used a Horseradish Peroxidase conjugated rabbit anti-goat antibody (1/100 dilution) (Jackson Immunoresearch Laboratories). Diaminobenzidine (Sigma) was used as a chromogen for 5 minutes. Sections were washed in aqua destillata and counterstained with hematoxylin. For tissue culture slides the same procedure was applied. In additional control experiments, blocking peptides or recombinant proteins were pre-incubated with the above-mentioned concentrations of antibodies to test specificity.

Statistical Analysis

Comparisons among three or more groups were made by a non-parametric Friedman ANOVA test, and those between two groups were made by a non-parametric Wilcoxon test for paired samples or Mann Whitney U test for unpaired samples. For survival analysis in the animal experiments a Gehan's Wilcoxon non-parametric survival test was used. All statistical analysis was performed using Statistica software (Statsoft Benelux, Groningen, The Netherlands). A value of $p<0.05$ was considered significant.

EXAMPLES

Example 1

Proinflammatory Cytokines Such as IL-1 and TNF-α Induce BMP-2, 6 and 7 Expression in Mesenchymal Cells In Vitro as Shown by Semi-Quantitative RT-PCR Patient synovial membrane (SM) biopsies were obtained by knee needle arthroscopy. Articular chondrocytes were obtained from knee joints postmortem within 12 hours of death. Periosteal biopsies were obtained from tibia postmortem within 12 hours of death. Tissues were digested overnight with 0.2% Collagenase (Life Technologies) in high glucose Dulbecco's modified Eagle's medium (DMEM, Life technologies) supplemented with 10% fetal bovine serum (FBS, BioWhittaker) and antibiotic-antimycotic solution (100 units/ml penicillin, 100 µg/ml sterptomycin, and 0.25 µg/ml amfotericin B, Life Technologies). After digest, cells were collected by centrifugation, washed twice and grown in high-glucose DMEM supplemented with FBS and antibiotics (growth medium) and allowed to adhere for 4 days. Non-adherent cells were subsequently removed by changing the medium. Cells were grown till confluence in monolayer in growth medium at 37° in a humidified atmosphere of 5% CO2, replacing the medium twice a week. At confluence cells were washed twice with calcium and magnesium free phosphate buffered saline (PBS) and harvested by treatment with trypsin-EDTA (0.25% Trypsin, 1 mM EDTA, Life Technologies) and replated at a 1/3 dilution. Between Passage 4 to Passage 8, confluent cells were stimulated with either IL1β (10 ng/ml, Biosource), TNFβ (10 ng/ml, Biosource) or IFN-gamma (100 U/ml, R&D Systems) for 24 hours. Total RNA was isolated using SNAP (Invitrogen) according to the manufacturer's instructions. 1,2 µg of total RNA was reverse transcribed using Thermoscript (Life Technologies). BMP-2, BMP-6, BMP-7 and TGFβ(1-3) were studied by semiquantitative polymerase chain reaction using β-actin as a house keeping gene. PCR products were demonstrated by ethidium bromide staining on 1.2% agarose gels and quantified using Imagemaster software (Pharmacia).

IL-1β and TNFα, but not IFN-γ result in upregulation of BMP-2, BMP-6 and BMP-7 gene expression whereas TGFβ1-3 expression levels were largely unaffected in expanded synovial fibroblast-like cells (FIG. 1A), expanded articular chondrocytes or expanded periosteal cells. Expression of BMP-4 was relatively low and not upregulated by IL1β or TNFα treatment. This demonstrates that mesenchymal cells, either from the synovium, the articular cartilage or the periost, can respond to an inflammatory stimulus by selectively upregulating specific BMPs.

Example 2

Proinflammatory Cytokines Such as IL-1 and TNF-α, and not INF-γ, Induce BMP-2 and BMP-6 in Mesenchymal Cells In Vitro as Shown by Real-Time Quantitative RT-PCR The influence of critical pro-inflammatory cytokines on BMP gene expression levels in FLS and immune cell cultures was further examined. FLS from both non-arthritic and arthritic joints were cultured in 6-well tissue culture plates in growth medium till confluence, and then stimulated for 24 hours with TNF-α (1 to 100 ng/ml), IL1β (1 to 100 ng/ml) or IFN-γ (10 to 1000 U/ml). As shown by real-time quantitative RT-PCR analysis, both BMP-2 and BMP-6 expression were up-regulated in the presence of TNF-α or IL-1β stimulation, but not in the presence of IFN-γ (FIG. 1). We consistently found BMP-2 and BMP-6 up-regulation by IL1β or TNF-α in all FLS cultures whether originating from non-arthritic, RA or SpA synovia (data from 12 different experiments in which FLS from 4 different donors were used). IL1β (10 ng/ml) treatment resulted in a mean 35.87 and 14.50 fold increase in BMP-2 and BMP-6 expression levels respectively (non-parametric Wilcoxon test $p<0.01$), TNF-α (10 ng/ml) incubation resulted in a mean 17.24 and 5.21 fold increase in BMP-2 and BMP-6 expression levels (non-parametric Wilcoxon test $p<0.01$ and $p<0.05$ respectively). BMP up-regulation by IL1β and TNF-α was dose dependent (data not shown).

We also studied BMP-4 regulation by TNF-α and IL-1β. No up-regulation of BMP-4 was seen in this experiment. BMP-4 was constitutively expressed in FLS cultures. No significant effects were seen on $TGFβ_1$, $TGFβ_2$ or $TGFβ_3$ expression levels (data not shown).

To extend these findings, BMP-2 and -6 protein were examined in FLS cultured on tissue culture slides. FLS were treated with IL1β (10 ng/ml) for 24 hours. BMP-2 and BMP-6 proteins were clearly detected after IL1β treatment using immunohistochemistry (FIG. 2).

Example 3

Heterotoic Bone Formation in the Enthesis in Spontaneous Arthritis in Aging Male DBA/1 Mice (SpAD), a Model of SpA, is a BMP Driven Process BMP-2, BMP-6 and BMP-7/OP-1 expression were studied by immunohistochemistry on paraffin embedded sections after acid or EDTA decalcification.

Specific BMPs were expressed in different stages of SpAD as demonstrated by immunohistochemistry (FIGS. 3 and 4). BMP-2 was typically expressed in early disease stages. The strongest BMP positivity was found in large round shaped and some of the proliferating fibroblast-like cells in the proliferative stage of ankylosing enthesitis (FIG. 3A-B). The expression pattern was not limited to the small fibrocartilage cells but is also found in fibroblast-like cells. In contrast, little or no BMP-2 expression was found in the later disease stages such as the differentiation into hyperthrophic chondrocytes or the replacement of these cells by woven bone (FIG. 3C-D). BMP-2 staining was cytoplasmic. No matrix staining was seen.

BMP-7/OP-1 in contrast was mainly expressed in chondroblast-like and prehypertrophic chondrocyte-like cells (FIG. 4). However no BMP-7/OP-1 positive cells were found in the hypertrophic zone. The proliferating fibroblast-like cells did not show BMP-7 positivity. BMP-7/OP-1 staining was cytoplasmic. No matrix staining was seen. BMP-6 positivity was mainly found in the hypertrophic-like chondrocytes (FIG. 4). Some BMP-6 positive cells were also found in the proliferative stage. In contrast to what was seen with BMP-2 and BMP-7/OP-1 antibodies, some cartilage matrix staining with BMP-6 was recognized. In the hypertrophic chondrocytes, a cytoplasmic staining pattern was recognized.

These results show that specific BMPs are expressed in pathological enthesial chondro- and osteogenesis, demonstrating that specific BMPs (BMP-2, -6 and -7) play a role in the similar process of enthesitis and ankylosis in SpA.

Example 4

Local Treatment of SpAD Mice Improves Enthesial Neochondro- and Osteogenesis 8 male DBA/1 mice were grouped at 12 weeks and checked daily for the appearance of SpAD. After onset of the clinical symptoms, the mice were either treated with two weekly injections of 5 µg Noggin-Fc chimeric molecule (R&D systems) or vehicum-control (PBS-0.5% serum albumine) into the affected toe. The amount of Noggin used was chosen on the basis of its high affinity for BMP-2 and BMP-4 (in vitro ED50 for 75 ng BMP2/4=0.3-1 µg Noggin). Mice were scored daily for clinical signs of arthritis. Three weeks after the onset of disease, mice were killed and hindpaws were processed for histology as described above. Histological assesment of the treated toes was made with a composite score taking into account cell proliferation, neochondrogenesis, neoosteogeneses, joint space bridging and ankylosis. We demonstrated a significant improvement in the mice treated with Noggin injections as compared to placebo controls.

Example 5

Spontaneous Arthritis in Aging Male DBA/1 Mice is Effectively Inhibited by Noggin cDNA Overexpression Mouse Noggin cDNA injections in aging male DBA/1 mice were used to overexpress Noggin in order to to inhibit BMP signaling in this model of Spondyloarthropathy. The mouse Noggin gene was cloned into the PCDNA 3.1 vector under the control of a Cytomegalovirus promotor.

Two different experiments were performed. In the first experiment microscopic anlysis was performed without knowledge of mouse identity or treatment group. The second experiment was performed with blinding during treatment, clinical observation and microscopic analysis.

Male DBA/1 mice from different litters were caged together (4 to 6 mice per cage) at the age of 11 weeks (first experiment) or 10 weeks (second experiment). Mouse Noggin cDNA plasmid injections (300 μg in the first experiment, 30 μg in the second experiment) were started at the time of grouped caging and continued every 3 weeks until the end of the experiment. As controls, empty vectors were used. The tibialis anterior muscle was used as injection site and injections were switched between right and left paw. The expression of the protein of interest in the muscle using this delivery method was demonstrated in preliminary experiments using β-galactosidase over-expression.

In the first experiment (7 animals per group) both clinical incidence and severity were significantly reduced as compared to control animals in Noggin cDNA treated mice (Gehan's Wilcoxon test p<0.03 and Mann Whitney U test p<0.01 respectively) (FIGS. 5 and 6). In the control vector treated group, 5 out of 7 animals developed signs of arthritis as compared to 1 out of 7 animals in the Noggin treated group. In the control animals the first signs of disease appeared in 1 animal at 16 weeks. In the Noggin treated group the first symptoms only appeared at an age of 23 weeks. At this time point, 4 out of 7 animals already showed arthritic toes in the control group. Animals in this experiment were sacrificed at the age of 24 weeks. Microscopic analysis confirmed the clinical observations (FIG. 7) (Mann Whitney test p<0.03). In all animals clinical signs of disease and abnormal histology were matching completely. In the Noggin treated animals the score of 1 was recorded in the affected mouse. In contrast scores in the control vector treated group, scores between 1 and 7 were recorded in affected mice. In the second experiment 17 animals were used, 8 in the Noggin cDNA treated group, 9 in the control group. As in the previous experiment both clinical incidence and severity were significantly reduced in the Noggin treated group as compared to controls (Gehan's Wilcoxon test p<0.02 and Mann-Whitney U test p<0.02) (FIGS. 5 and 6). In the control vector treated group 8 out 9 animals developed symptoms of arthritis. In contrast, in the Noggin cDNA treated animals, only 2 out of 8 animals were affected. In the control group first symptoms were recorded at the age of 17 weeks. In the Noggin cDNA treated mice first symptoms were seen at the age of 20 weeks. At this time point 5 out of 9 animals showed signs of artritis in the control vector treated group. In the 2 affected animals in the Noggin treatment group clinical disease scores were 2 and 3. In contrast, clinical severity scores in the affected animals in the control group ranged between 1 and 4.

---

We claim:

1. A method for reducing the incidence of or treating Spondyloarthropathic (SpA) enthesitis in a mammal comprising the step of administering to said mammal an amount of noggin effective to reduce the incidence of or to treat SpA enthesitis.

2. The method according to claim 1, wherein said SpA enthesitis is psoriatic arthritis.

3. The method according to claim 1, wherein said noggin is delivered either systemically or locally with an acceptable pharmaceutical carrier.

4. The method according to claim 1, wherein said noggin is co-administered with one or more additional therapeutic agents.

* * * * *

UNITED STATES PATENT AND TRADEMARK OFFICE
CERTIFICATE OF CORRECTION

PATENT NO. : 7,371,725 B2 Page 1 of 1
APPLICATION NO. : 10/503751
DATED : May 13, 2008
INVENTOR(S) : Frank Luyten and Rik Lories It is certified that error appears in the above-identified patent and that said Letters Patent is hereby corrected as shown below:

Column 19, Line 63, replace "BMIP-2" with --BMP-2--.

Column 21, in TABLE 1, (SEQ ID NO:4), replace "GAAGTAGAGGACGGAGATGGG" with --GAAGTAGAGGACGGAGATGGC--.

Column 25, Line 5, replace "TNFβ" with --TNFα-- .

Column 26, Line 3, replace "Heterotoic" with --Heterotopic--.

Column 27, Line 13, replace "anlysis" with --analysis--.

Column 28, Line 28, replace "artritis" with --arthritis--.

Signed and Sealed this

Fourteenth Day of October, 2008

JON W. DUDAS
*Director of the United States Patent and Trademark Office*